United States Patent
Fukuda et al.

(10) Patent No.: US 8,303,800 B2
(45) Date of Patent: Nov. 6, 2012

(54) ELECTROCHEMICAL SENSOR DEVICE AND ELECTROCHEMICAL MEASURING METHOD USING THE SAME

(75) Inventors: Junji Fukuda, Tsukuba (JP); Hiroaki Suzuki, Tsukuba (JP); Kentaro Okamura, Kawasaki (JP); Masatoshi Hashimoto, Tsuchiura (JP); Takahisa Anada, Sendai (JP); Hideki Kuramitsu, Toyama (JP); Go Tazaki, Tsukuba (JP)

(73) Assignees: University of Tsukuba, Ibaraki (JP); Kuraray Co., Ltd., Okayama (JP)

( * ) Notice: Subject to any disclaimer, the term of this patent is extended or adjusted under 35 U.S.C. 154(b) by 308 days.

(21) Appl. No.: 12/733,533

(22) PCT Filed: Jul. 30, 2008

(86) PCT No.: PCT/JP2008/063667
§ 371 (c)(1),
(2), (4) Date: Mar. 5, 2010

(87) PCT Pub. No.: WO2009/031375
PCT Pub. Date: Mar. 12, 2009

(65) Prior Publication Data
US 2011/0042237 A1    Feb. 24, 2011

(30) Foreign Application Priority Data
Sep. 7, 2007   (JP) ................................ 2007-233358

(51) Int. Cl.
*G01F 1/64* (2006.01)
(52) U.S. Cl. .................... 205/775; 204/400; 204/289
(58) Field of Classification Search .............. 205/775; 204/400, 502–508, 289; 422/502–508
See application file for complete search history.

(56) References Cited

U.S. PATENT DOCUMENTS

| 5,427,663 | A  | * | 6/1995  | Austin et al. ................ 204/549 |
| 6,159,353 | A  | * | 12/2000 | West et al. ................... 204/601 |
| 8,137,514 | B2 | * | 3/2012  | Kim ............................. 204/271 |
| 2002/0170825 | A1 | * | 11/2002 | Lee et al. .................... 204/455 |
| 2005/0095699 | A1 | * | 5/2005  | Miyauchi et al. .......... 435/299.1 |
| 2009/0294291 | A1 | * | 12/2009 | Voldman et al. ............ 204/547 |

FOREIGN PATENT DOCUMENTS

JP            A-1-174960          7/1989
(Continued)

OTHER PUBLICATIONS

"Frequently asked Questions about Conductivity", published by Mettler-Toledo ("faq_con_Mettler").*
English translation of May 20, 2010 International Preliminary Report on Patentability issued in International Application No. PCT/JP2008/063667.

(Continued)

*Primary Examiner* — J. Christopher Ball
*Assistant Examiner* — Steven Rosenwald
(74) *Attorney, Agent, or Firm* — Oliff & Berridge, PLC

(57) ABSTRACT

Provided is an electrochemical sensor device capable of micromachining a channel while maintaining its measurement sensitivity and of reliably quantitating an analyte in a trace amount of a sample. An electrochemical sensor device includes: a channel portion formed in a substrate; and working electrodes for subjecting an analyte in a solution flowing in the channel portion to electrochemical measurement, the electrochemical sensor device includes a plurality of measuring portions individually provided with the working electrodes, and each of the working electrodes has a plurality of conductive protrusion portions formed to protrude from a bottom surface of each of the measuring portions.

9 Claims, 21 Drawing Sheets

FOREIGN PATENT DOCUMENTS

| | | | |
|---|---|---|---|
| JP | 1-174960 | * | 11/1989 |
| JP | A-2000-9679 | | 1/2000 |
| JP | A-2000-97899 | | 4/2000 |
| JP | A-2002-170557 | | 6/2002 |
| JP | A-2004-85392 | | 3/2004 |
| JP | A-2006-119051 | | 5/2006 |
| JP | A-2006-201080 | | 8/2006 |
| WO | 2007/059194 | * | 5/2007 |

OTHER PUBLICATIONS

Satoh et al.; "Micro Fluidic Transport System Which Operates Via Manipulation of Interfacial Tension;" *The Papers of Technical Meeting on Chemical Sensor, IEE Japan*; 2003; pp. 149-154. (w/ abstract).

International Search Report for International Application No. PCT/JP2008/063667, issued Aug. 26, 2008.

* cited by examiner

FIG.18
|  | FLAT | φ30 | φ20 | φ10 |
|---|---|---|---|---|
| PILLAR DIAMETER (μm) | — | 30 | 20 | 10 |
| PILLAR INTERVAL (μm) | — | 30 | 20 | 10 |
| NUMBER OF PILLARS | — | 36 | 143 | 550 |
| ELECTRODE SURFACE AREA (mm²) | 0.25 | 0.42 | 0.7 | 1.11 |
| SURFACE AREA RATIO | 1 | 1.7 | 2.8 | 4.4 |
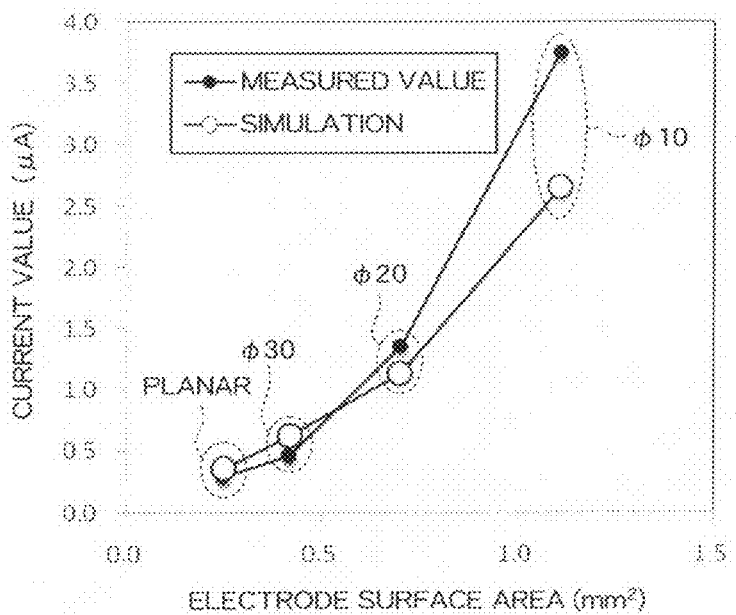
FIG.19
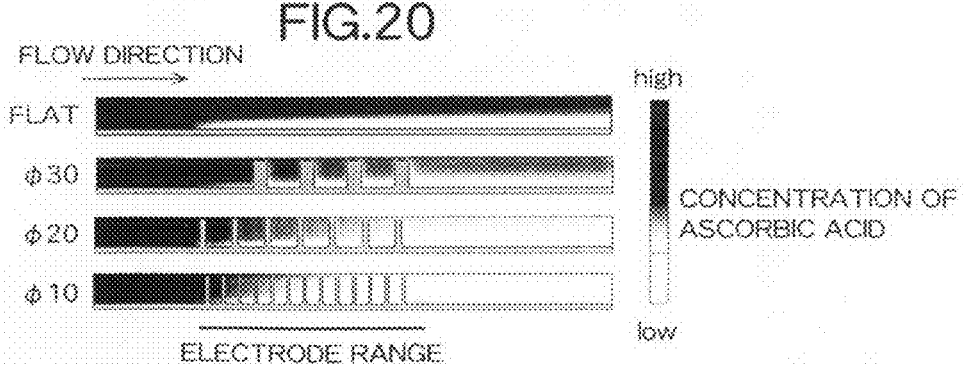
FIG.20

FIG.21
(A)
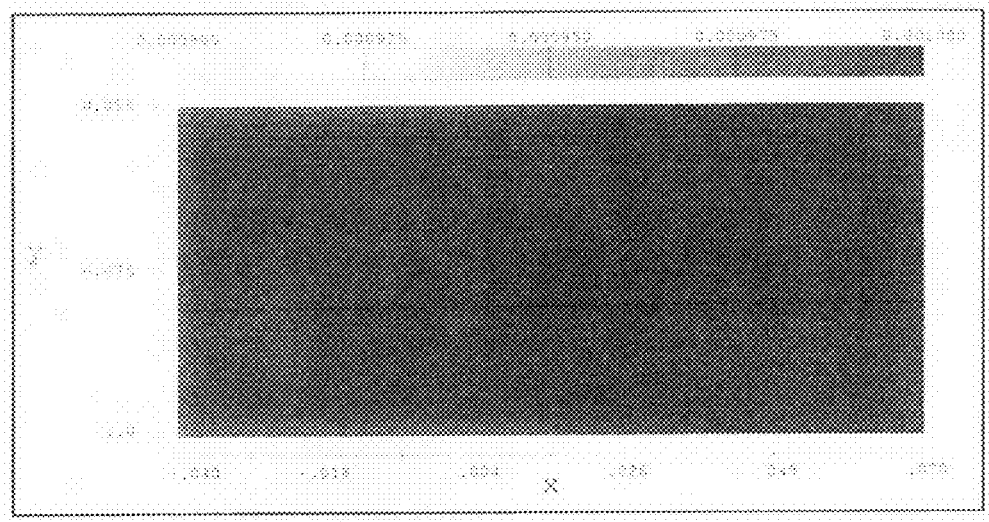
(B)
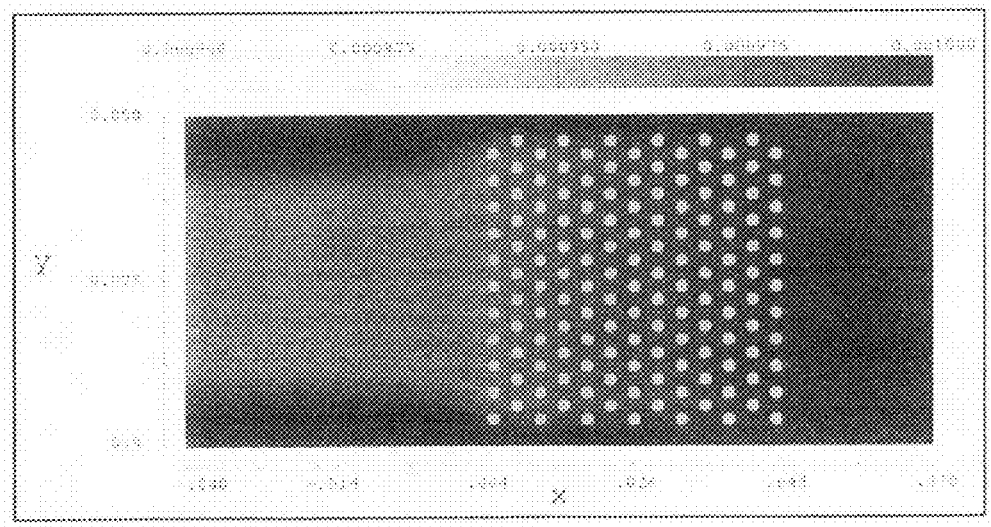

FIG.22
(A)
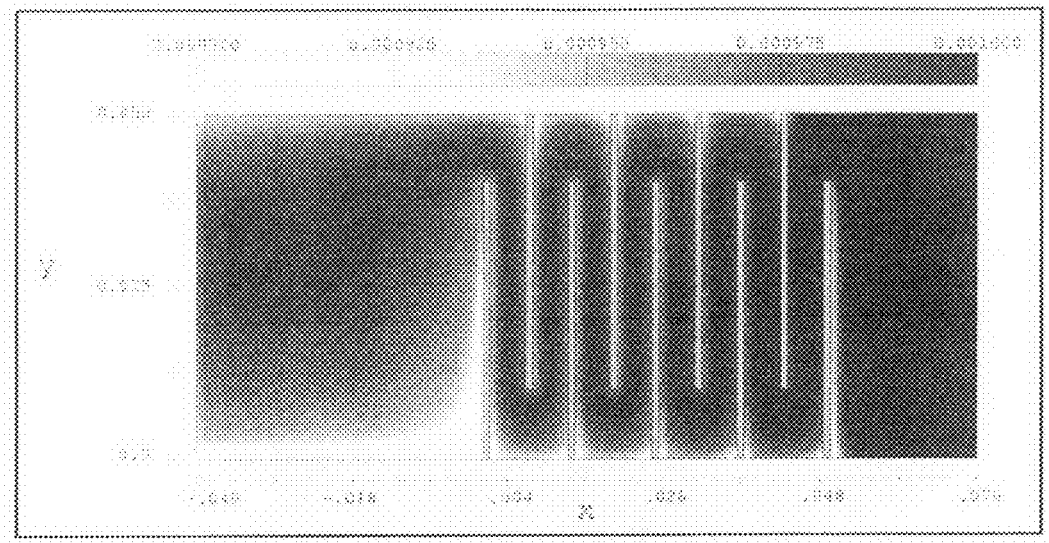
(B)
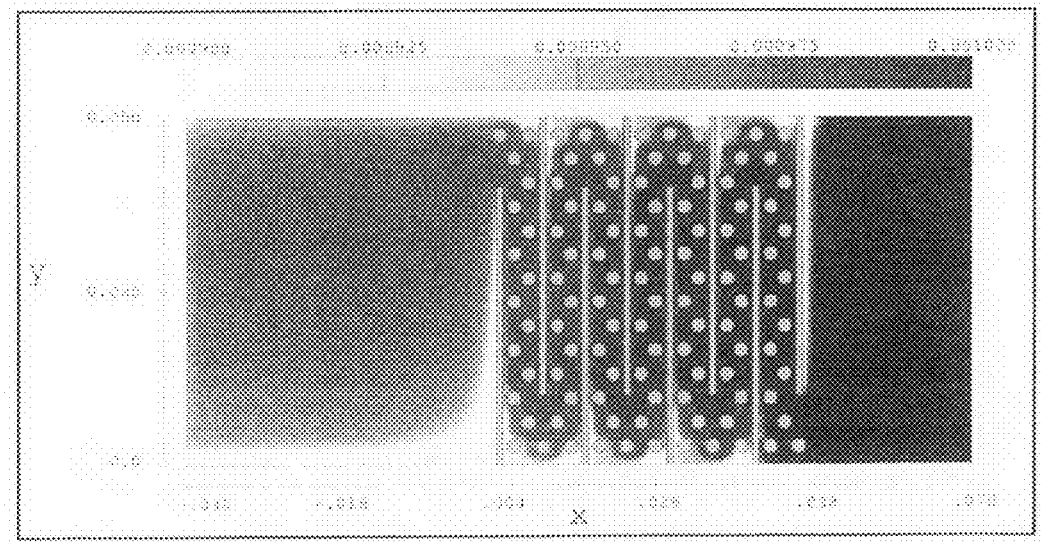

FIG.23
(A)
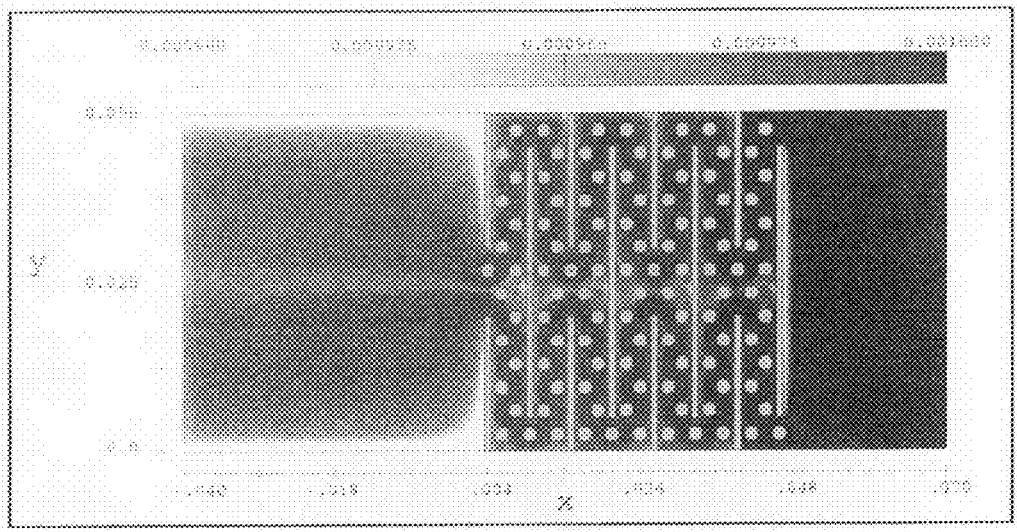
(B)
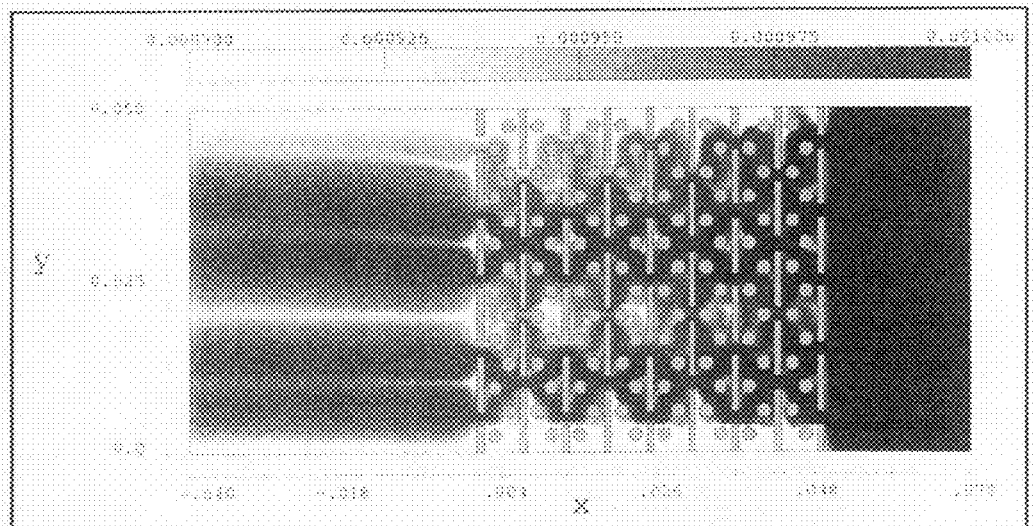

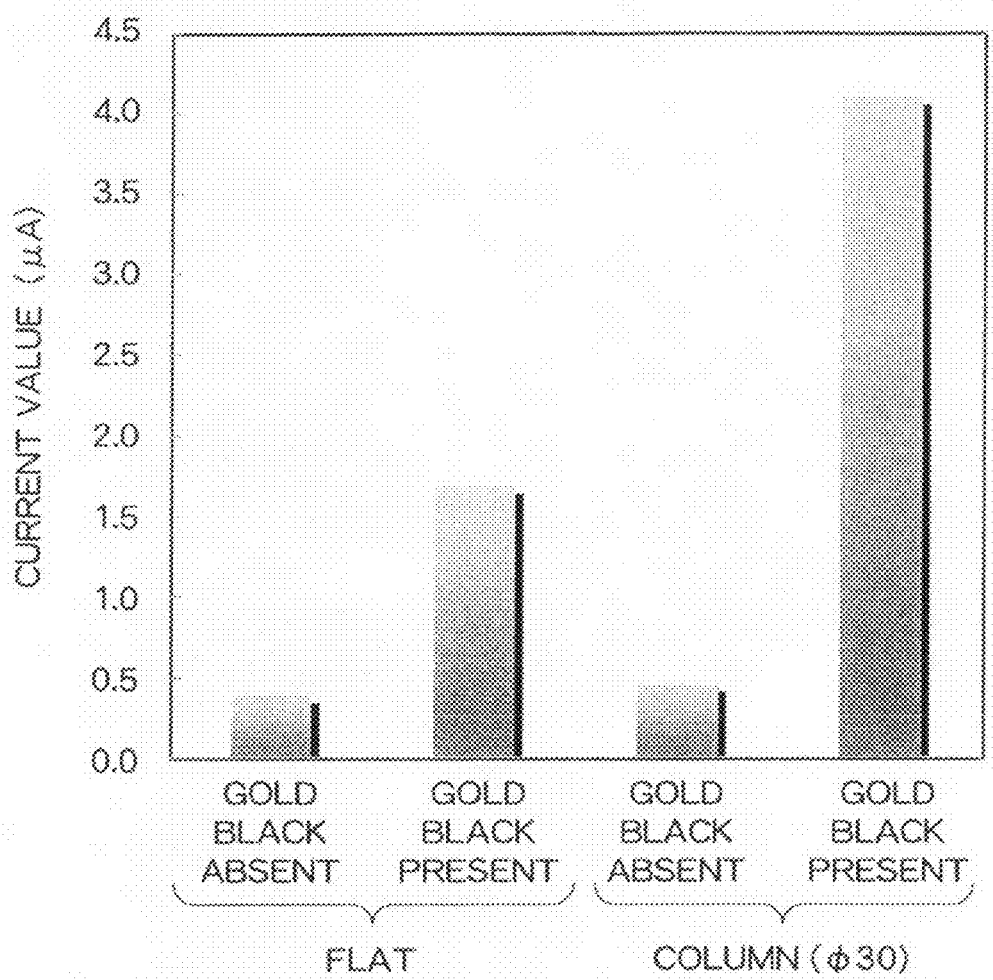

ELECTROCHEMICAL SENSOR DEVICE AND ELECTROCHEMICAL MEASURING METHOD USING THE SAME

TECHNICAL FIELD

The present invention relates to an electrochemical sensor device and an electrochemical measuring method using the same, in particular, an electrochemical sensor device including a working electrode disposed in a microchannel and an electrochemical measuring method using the same.

BACKGROUND ART

There has been conventionally provided a sensor including a microchannel through which a solution flows, and having a working electrode for subjecting a substance in the solution to electrochemical measurement, the working electrode being formed in a planar shape on the bottom surface of the channel (for example, Patent Document 1).

In addition, Patent Document 2 describes a biosensor including, on an upstream side of a planar working electrode, a minute protrusion for removing an interfering substance in a biological sample, the minute protrusion having a surface modified with a conductive material. Patent Document 2 described above also describes that simultaneous measurement for two components can be achieved with the working electrode and the minute protrusion as electrodes. In addition, Patent Document 3 describes a biosensor including, on the upstream side of a planar working electrode, a minute protrusion formed of a thermoplastic resin.

Patent Document 1: JP 2000-9679 A
Patent Document 2: JP 2000-97899 A
Patent Document 3: JP 2006-201080 A

DISCLOSURE OF THE INVENTION

Problems to be Solved by the Invention

However, for example, when the amount of a sample containing an analyte as a measuring object is very small and the amount of the analyte in the sample is also very small, it has not been possible to quantitate the analyte with the above-mentioned conventional sensor in some cases.

That is, when the amount of a sample is very small, the volume of a channel through which the sample flows must be reduced to the greatest extent possible. However, in the case of the above-mentioned conventional sensor in which the working electrode is of a planar shape along the bottom surface of the channel, the surface area of the working electrode is reduced in correspondence with the micrifying of the channel, and hence measurement sensitivity is reduced. Accordingly, the micrifying of the channel has had limitations. The problem has arisen also in the planar working electrode provided with the minute protrusion on its upstream side. In addition, the minute protrusion is disposed in the channel in addition to the working electrode, and hence the micrifying of the channel has had limitations.

In addition, in order for the concentration of an analyte to be accurately reflected in a current value measured with a working electrode, the concentration of the analyte in a sample contacting the working electrode and a current value measured in correspondence with the concentration each preferably fall within a specific range. On the other hand, for example, when the analyte is a disease marker, the concentration of the analyte in a sample collected from a patient significantly exceeds the above-mentioned specific range in some cases.

Therefore, when a sample is directly subjected to measurement with the above-mentioned conventional sensor, a current value deviates significantly from the above-mentioned specific range. Accordingly, no accurate results can be obtained and the sample or a reagent, which is rare, is exhausted in some cases.

The present invention has been made in view of the above-mentioned problems, and an object of the present invention is to provide an electrochemical sensor device capable of micrifying a channel while maintaining its measurement sensitivity, and of reliably quantitating an analyte in a trace amount of a sample, and an electrochemical measuring method using the device.

Means for Solving the Problems

An electrochemical sensor device according to an embodiment of the present invention for solving the above-mentioned problems is characterized by including: a channel portion formed in a substrate; and working electrodes for subjecting an analyte in a solution flowing in the channel portion to electrochemical measurement, in which: the channel portion includes a first stem portion through which a first solution flows and a second stem portion through which a second solution flows, and a plurality of measuring portions extending toward downstream sides of the first stem portion and the second stem portion and provided individually with the working electrodes; the plurality of measuring portions include a confluent portion through which a mixed solution of the first solution and the second solution flows, the confluent portion extending from a portion where a branch portion branching from the first stem portion and a branch portion branching from the second stem portion merge with each other toward a downstream side, a first independent portion through which the first solution flows, the first independent portion extending toward the downstream side of the first stem portion without merging with any other channel, and a second independent portion through which the second solution flows, the second independent portion extending toward the downstream side of the second stem portion without merging with any other channel; and the working electrodes each have a plurality of conductive protrusion portions formed to protrude from a bottom surface of the measuring portion. According to the present invention, there can be provided an electrochemical sensor device capable of micrifying a channel while maintaining its measurement sensitivity and of reliably quantitating an analyte in a trace amount of a sample.

Further, the plurality of protrusion portions may include a plurality of plate-like protrusion portions each formed in a plate-like shape and crossing the measuring portion to block part of a flow in a longitudinal direction of the measuring portion and a plurality of columnar protrusion portions each formed in a columnar shape, the plurality of plate-like protrusion portions may include a pair of plate-like protrusion portions disposed to partly overlap each other in the longitudinal direction, and the plurality of columnar protrusion portions may be disposed between the pair of the plate-like protrusion portions. Further, in this case, one of the pair of the plate-like protrusion portions may extend from one side surface of the measuring portion and the other of the pair may extend from the other side surface of the measuring portion. Further, in those cases, the electrochemical sensor device may include: a pair of upstream-side dam portions extending from one side surface and the other side surface of each of the measuring portions to block part of a flow in a longitudinal direction of the measuring portion in an upstream end portion of the working electrode; and a pair of downstream-side dam portions extending from the one side surface and other side surface of the measuring portion to block part of the flow in the longitudinal direction of the measuring portion in a downstream end portion of the working electrode. In this way, an analyte in a trace amount of a sample can be more reliably quantitated.

An electrochemical measuring method according to an embodiment of the present invention for solving the above-mentioned problems is characterized by subjecting the analyte in the solution flowing through each of the measuring portions to electrochemical measurement with any one of the above-mentioned electrochemical sensor devices. According to the present invention, there can be provided an electrochemical measuring method by which an analyte in a trace amount of a sample can be reliably quantitated.

Further, the electrochemical measuring method may include: preparing calibration data showing a correlation between a plurality of concentrations of the analyte and current values corresponding to the respective plurality of concentrations; causing the first solution containing the analyte to flow into the first stem portion and causing the second solution free of the analyte to flow into the second stem portion; and determining a concentration of the analyte in the first solution on the basis of current values measured for the confluent portion, the first independent portion, and the second independent portion with the working electrodes, and the calibration data. In this way, an analyte in a trace amount of a sample can be more reliably quantitated.

BRIEF DESCRIPTION OF THE DRAWINGS

FIG. 18 is a view for describing conditions for the working electrode produced in the embodiment of the present invention.

FIG. 19 is a view for describing comparison between measured results and simulation results in the embodiment of the present invention.

FIG. 20 is a view for describing an example of a concentration distribution in a side view obtained in the simulations of the embodiment of the present invention.

FIG. 21 are each a view for describing an example of a concentration distribution in a planar view obtained in the simulation of the embodiment of the present invention.

FIG. 22 are each a view for describing another example of the concentration distribution in a planar view obtained in the simulation of the embodiment of the present invention.

FIG. 23 are each a view for describing still another example of the concentration distribution in a planar view obtained in the simulation of the embodiment of the present invention.

FIG. 29 is a view for describing an effect of the formation of gold black in the embodiment of the present invention.

BEST MODE FOR CARRYING OUT THE INVENTION

Hereinafter, an electrochemical sensor device according to an embodiment of the present invention (hereinafter referred to as "the device") and an electrochemical measuring method using the device (hereinafter referred to as "the method") are described. It should be noted that the present invention is not limited to examples described in the embodiment.

Figure 1:
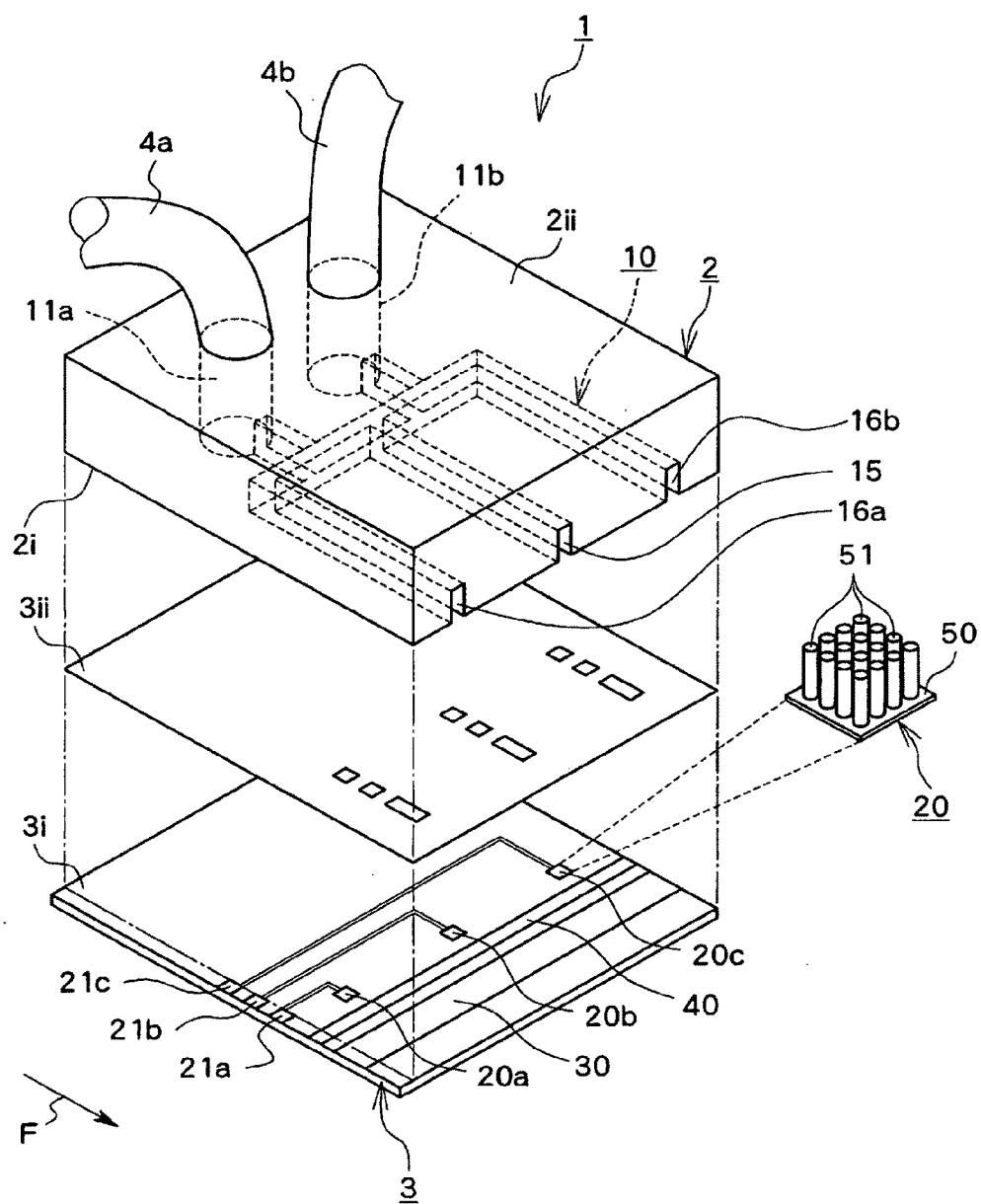
FIG. 1 is a view for describing an example of an electrochemical sensor device according to an embodiment of the present invention.

FIG. 1 is a view for describing an example of the device 1. As illustrated in FIG. 1, the device 1 includes a channel substrate 2 in which a microchannel portion 10 as a microchannel through which a solution flows is formed, and an electrode substrate 3 provided with three working electrodes 20a, 20b, and 20c each used for subjecting an analyte in the solution to electrochemical measurement.

It should be noted that the direction indicated by an arrow F represents the downstream side direction of the microchannel portion 10. In addition, when the device 1 has a plurality of identical parts in the following description, the plurality of parts are described by being provided with symbols obtained by combining the same numeral and lower-case alphabet characters that are different from each other (for example, "the working electrodes 20a, 20b, and 20c") in some cases. It should be noted that when there is no particular need to discriminate a plurality of parts from each other, the parts are described by being provided with the numeral alone while omitting the alphabet characters (for example, "the working electrodes 20").

As illustrated in FIG. 1, the microchannel portion 10 is formed in a lower side surface (lower surface 2i) of the channel substrate 2, opposite to the electrode substrate 3. In addition, an electrode system including the working electrodes 20 is formed in a portion corresponding to part of the microchannel portion 10, which is a portion of the upper side surface (upper surface 3i) of the electrode substrate 3 opposite to the channel substrate 2. the device 1 can be constituted by joining the channel substrate 2 and the electrode substrate 3.

Figure 2:
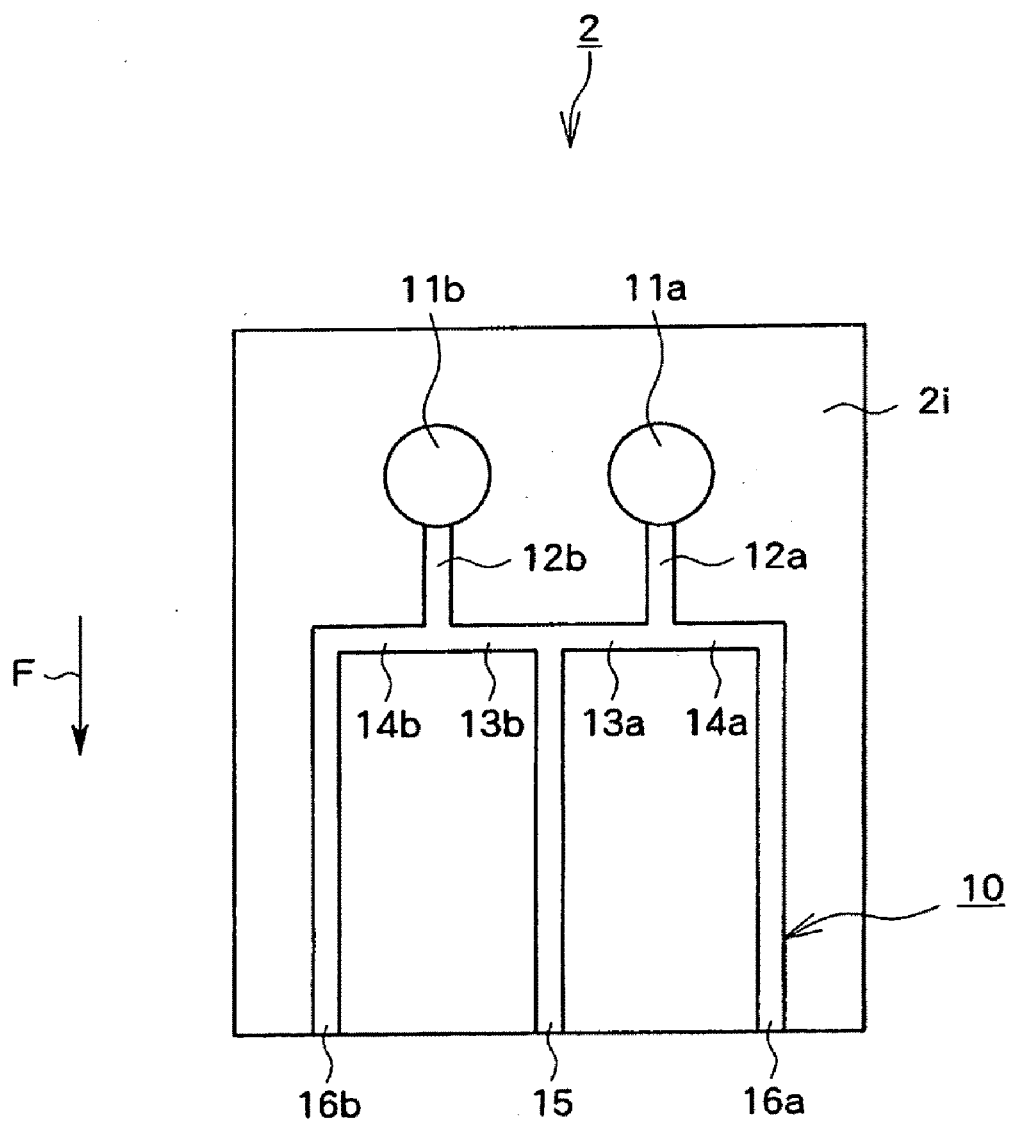
FIG. 2 is a plan view of an example of a channel substrate according to the embodiment of the present invention.
Figure 3:
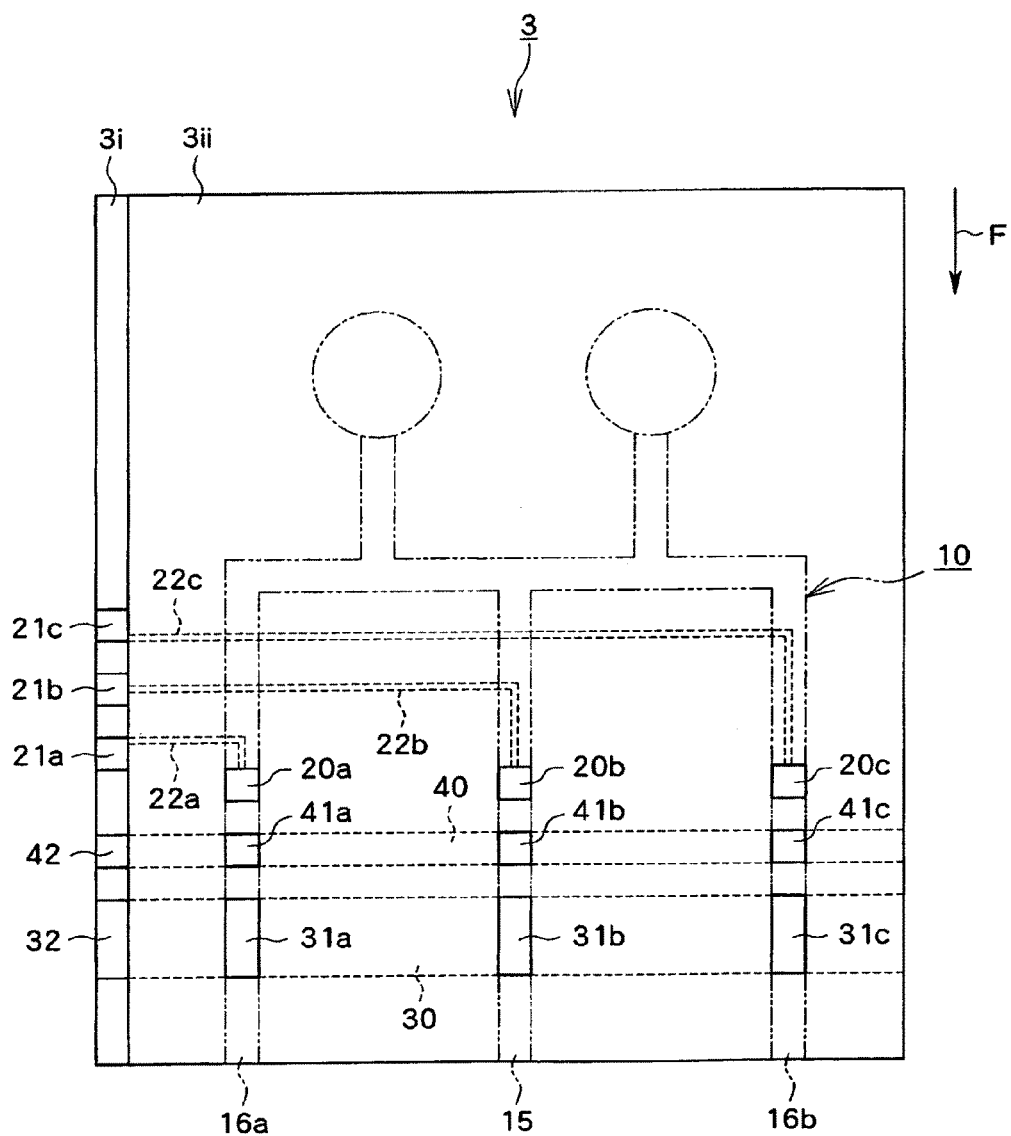
FIG. 3 is a, plan view of an example of an electrode substrate according to the embodiment of the present invention.

FIG. 2 is a plan view illustrating the channel substrate 2 observed from the side of the lower surface 2i. FIG. 3 is a plan view illustrating the electrode substrate 3 observed from the side of the upper surface 3i. In FIG. 3, the position at which the microchannel portion 10 is disposed is represented with a chain double-dashed line.

As illustrated in FIGS. 1 and 2, the microchannel portion 10 has a first inflow portion 11a and a second inflow portion 11b each used for allowing a solution to flow from the outside of the microchannel portion 10 to the inside of the microchannel portion, the first and second inflow portions being formed at end portions on the upstream side of the microchannel portion 10. A circular hole penetrating the channel substrate 2 is formed in each of the first inflow portion 11a and the second inflow portion 11b.

In addition, as illustrated in FIG. 1, a first inflow tube 4a and a second inflow tube 4b for guiding the solution from the outside of the device 1 into the microchannel portion 10 are connected to portions at which the first inflow portion 11a and the second inflow portion 11b open in a surface 2ii on the upper side of the channel substrate 2, respectively. The first inflow tube 4a and the second inflow tube 4b can each be constituted of, for example, a tube made of silicone rubber.

In addition, as illustrated in FIG. 2, the microchannel portion 10 has a first stem portion 12a and a second stem portion 12b extending from the first inflow portion 11a and the second inflow portion 11b, respectively, toward the downstream side so as to be parallel and adjacent to each other.

Further, the microchannel portion 10 has a plurality of branch portions 13 and 14 branching from the first stem portion 12a and the second stem portion 12b. That is, a first confluent branch portion 13a and a first independent branch portion 14a, each extending at right angles from the downstream end of the first stem portion 12a in a branched fashion toward the second stem portion 12b and away from the second stem portion 12b, respectively, are formed. In addition, a second confluent branch portion 13b and a second independent branch portion 14b, each extending at right angles from the downstream end of the second stem portion 12b in a branched fashion toward the first stem portion 12a and away from the first stem portion 12a, respectively, are formed. The downstream ends of the first confluent branch portion 13a and the second confluent branch portion 13b merge with each other at a position between the first stem portion 12a and the second stem portion 12b.

In addition, as illustrated in FIGS. 1 to 3, the microchannel portion 10 has a plurality of measuring portions 15 and 16 extending toward the downstream sides of the first stem portion 12a and the second stem portion 12b and individually provided with the working electrodes 20. That is, the microchannel portion 10 has a confluent portion 15 extending toward a downstream side from the portion where the first confluent branch portion 13a and the second confluent branch portion 13b merge with each other. The confluent portion 15 extends toward the downstream side while bending at right angles relative to each of the first confluent branch portion 13a and the second confluent branch portion 13b. In addition, the microchannel portion 10 has a first independent portion 16a and a second independent portion 16b extending from the downstream ends (end portions outside the width direction of the channel substrate 2) of the first independent branch portion 14a and the second independent branch portion 14b, respectively, further toward the downstream side so as to be parallel to the confluent portion 15 without merging with any other channel.

The confluent portion 15, the first independent portion 16a, and the second independent portion 16b constitute the downstream end portion of the microchannel portion 10, and the downstream ends of each of them open in the downstream end of the channel substrate 2.

A material of which the channel substrate 2 is constituted is not particularly limited, and an arbitrary material can be used depending on purposes. For example, a synthetic resin can be preferably used. For example, an acrylic resin such as polymethyl methacrylate or a methyl methacrylate-styrene copolymer, a styrene-based resin such as polystyrene, an olefin-based resin such as cycloolefin, an ester-based resin such as polyethylene terephthalate or polylactic acid, a silicone-based resin such as polydimethylsiloxane, or a polycarbonate resin can be preferably used as the synthetic resin.

In addition, a method of producing the channel substrate 2 is not particularly limited, and an arbitrary method can be employed depending on purposes. For example, a method involving producing a die of a shape corresponding to the microchannel portion 10 by means of photolithography and molding a synthetic resin such as a silicone-based resin with the die can be preferably employed.

Meanwhile, as illustrated in FIGS. 1 and 3, the first working electrode 20a is formed at a position corresponding to a midcourse portion of the first independent portion 16a, the second working electrode 20b is formed at a position corresponding to a midcourse portion of the confluent portion 15, and the third working electrode 20c is formed at a position corresponding to a midcourse portion of the second independent portion 16b on the upper surface 3i of the electrode substrate 3.

That is, in the device 1, the working electrodes 20 are formed individually in each of the first independent portion 16a, the confluent portion 15, and the second independent portion 16b of the microchannel portion 10. In addition, the three working electrodes 20a, 20b, and 20c are formed at positions having the same distance from the upstream ends of the first independent portion 16a, the confluent portion 15, and the second independent portion 16b, respectively, and are disposed at the same position in the flow direction of the microchannel portion 10 (that is, linearly in the width direction of the electrode substrate 3).

Further, three working electrode pads 21a, 21b, and 21c corresponding to the three working electrodes 20a, 20b, and 20c, respectively, and three lead wires 22a, 22b, and 22c connecting the corresponding three working electrodes 20a, 20b, and 20c, and the three working electrode pads 21a, 21b, and 21c, respectively, are formed at an end portion on one side in the width direction of the electrode substrate 3 on the upper surface 3i of the electrode substrate 3.

In addition, one belt-shaped reference electrode belt 40 formed of a conductive material and extending over the three measuring portions (the first independent portion 16a, the confluent portion 15, and the second independent portion 16b) is formed in the width direction of the electrode substrate 3 on the downstream sides of the working electrodes 20 on the upper surface 3i of the electrode substrate 3. Further, one belt-shaped counter electrode belt 30 formed of a conductive material and extending over the two measuring portions 15 and 16 is formed in the width direction of the electrode substrate 3 so as to be parallel to the reference electrode belt 40 on the downstream side of the reference electrode belt 40 on the upper surface 3i of the electrode substrate 3.

In addition, as illustrated in FIGS. 1 and 3, portions of the upper surface 3i of the electrode substrate 3, except for the working electrodes 20, the working electrode pads 21, portions of the reference electrode belt 40 and the counter electrode belt 30 overlapping the measuring portions 15 and 16, and end portions of the reference electrode belt 40 and the counter electrode belt 30 that are on one side in the width direction of the electrode substrate 3, are covered with an insulating film 3ii formed of an insulating material. As a result, parts of the reference electrode belt 40 and the counter electrode belt 30 are exposed at the portions of the reference electrode belt 40 and the counter electrode belt 30 overlapping the measuring portions 15 and 16 not covered with the insulating film 3ii so that reference electrodes 41 and counter electrodes 31 may be formed, respectively. It should be noted that the insulating film 3ii can be formed of polyimide or the like in, for example, the case where the electrode substrate 2 is made of glass.

As a result, as illustrated in FIG. 3, a first electrode system formed of the first working electrode 20a, a first reference electrode 41a, and a first counter electrode 31a is formed in the first independent portion 16a in the device 1. In addition, a second electrode system formed of the second working electrode 20b, a second reference electrode 41b, and a second counter electrode 31b is formed in the confluent portion 15. In addition, a third electrode system formed of the third working electrode 20c, a third reference electrode 41c, and a third counter electrode 31c is formed in the second independent portion 16b. That is, the working electrodes 20, the reference electrodes 40, and the counter electrodes 30 are formed individually in each of the three measuring portions 15, 16a, and 16b.

In addition, the three working electrode pads 21a, 21b, and 21c, one reference electrode pad 42, and one counter electrode pad 32 are formed at the end portion on one side in the width direction of the electrode substrate 3. It should be noted that the reference electrode pad 42 and the counter electrode pad 32 are end portions of the reference electrode belt 40 and the counter electrode belt 30, respectively, on one side in the width direction of the electrode substrate 3 not covered with the insulating film 3ii.

One characteristic of the device 1 is that each of the three working electrodes 20a, 20b, and 20c is formed so as to be of a concavo-convex shape including a group of protrusion portions 51 as illustrated in FIG. 1. That is, the working electrodes 20 each have a plurality of conductive protrusion portions 51 formed so as to protrude in each of the measuring portions 15 and 16. In addition, the working electrodes 20 each have a conductive base 50 formed along the inner surface of each of the measuring portions 15 and 16. In the example illustrated in FIG. 1, the base 50 is formed in a planar shape in the upper surface 3i of the electrode substrate 3, and the protrusion portions 51 are each formed in a cylindrical shape protruding upward from the base 50. The base 50 and the protrusion portions 51 are electrically connected through their conductive surfaces, and integrally constitute any one of the working electrodes 20. It should be noted that although the third working electrode 20c is illustrated as one of the three working electrodes 20a, 20b, and 20c in an enlarged fashion in FIG. 1 for convenience of description, the other two working electrodes 20a and 20b are each similarly constituted of the base 50 and the plurality of protrusion portions 51.

Figure 4:
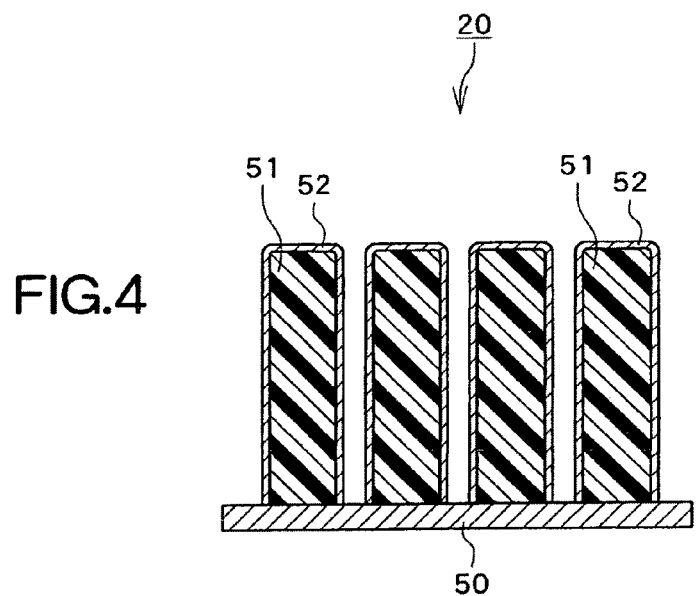
FIG. 4 is a sectional view of an example of a working electrode according to the embodiment of the present invention.

FIG. 4 illustrates a sectional view when anyone of the working electrodes 20 is cut along a plane passing part of the protrusion portions 51. As illustrated in FIG. 4, each of the plurality of protrusion portions 51 is formed as a space structure standing on the surface of the base 50.

That is, the protrusion portions 51 of the first working electrode 20a, the protrusion portions 51 of the second working electrode 20b, and the protrusion portions 51 of the third working electrode 20c extend in the first independent portion 16a, the confluent portion 15, and the second independent portion 16b, in their respective channel height directions (directions perpendicular to the upper surface 3i of the electrode substrate 3).

In addition, as illustrated in FIGS. 1 and 3, the widths (lengths in the directions perpendicular to the longitudinal directions of the measuring portions 15 and 16) of the bases 50 of the first working electrode 20a, the second working electrode 20b, and the third working electrode 20c are substantially identical to the widths of the first independent portion 16a, the confluent portion 15, and the second independent portion 16b, respectively. In addition, the group of protrusion portions 51 is formed over an entire region in the width direction of the base 50.

In addition, the base 50 is formed as a thin film formed of a conductive electrode material. On the other hand, as illustrated in FIG. 4, the surfaces of the protrusion portions 51 are each constituted of an electrode thin film 52 formed of an electrode material. That is, the working electrodes 20 each have one electrode surface in which the base 50 and the electrode thin film 52 formed on the surface of each of the protrusion portions 51 are integrated by being electrically connected. As a result, the working electrodes themselves are each formed so as to be of an integrated concavo-convex shape constituted of the base 50 and the protrusion portions 51, and each have an electrode surface having a large surface area based on the concavo-convex shape.

The shape, size, and number of the protrusion portions 51 are not particularly limited as long as the area of the electrode surface of each of the working electrodes 20 can be effectively increased. That is, the shape of each of the protrusion portions 51 is not limited to a cylindrical shape, and can be a columnar shape such as a polygonal columnar shape, a conical shape, or a polygonal pyramid shape. The diameter of each of the columnar protrusion portions 51 (the diameter of a section when the protrusion portions 51 is of a cylindrical shape or the diagonal length of a sectional polygon when the protrusion portions 51 is of a polygonal columnar shape) can be set to fall within, for example, the range of 1 to 300 μm, preferably 1 to 100 μm, more preferably 5 to 50 μm, or particularly preferably 10 to 30 μm. The aspect ratio of each of the columnar protrusion portions 51 (ratio of a height to a diameter) is preferably set to, for example, about 1 to 10.

In addition, the shape of the protrusion portions 51 is not limited to a columnar shape, and can be, for example, a plate-like shape. In addition, the plurality of protrusion portions 51 different from each other in shape can be formed on any one of the bases 50.

The height of the protrusion portions 51 can be set to fall within, for example, the range of 10 to 300 µm, preferably 10 to 100 µm, or more preferably 10 to 50 µm. In addition, an interval between the adjacent protrusion portions 51 can be appropriately set depending on purposes to such an extent that the solution can flow between the protrusion portions 51.

A material of which the electrode substrate 3 is constituted is not particularly limited, and an arbitrary material can be used depending on purposes. For example, a glass or a synthetic resin can be preferably used. For example, an acrylic resin such as polymethyl methacrylate or a methyl methacrylate-styrene copolymer, a styrene-based resin such as polystyrene, an olefin-based resin such as cycloolefin, an ester-based resin such as polyethylene terephthalate or polylactic acid, a silicone-based resin such as polydimethylsiloxane, or a polycarbonate resin can be preferably used as the synthetic resin.

An electrode material of which the working electrodes 20 (electrode surfaces each including the base 50 and the electrode thin films 52), the working electrode pads 21, the lead wires 22, the counter electrode belt 30, and the reference electrode belt 40 (see FIGS. 1 and 3) are each constituted is not particularly limited as long as the material has conductivity, and an arbitrary material selected from materials each having conductivity, such as a metal, a metal oxide, and carbon can be used depending on purposes. To be specific, a noble metal having a high oxygen overvoltage such as gold, platinum, or silver can be preferably used. In addition, for example, gold black or platinum black can be formed on the surface of each of the working electrodes 20.

A polarizable material having low corrosiveness such as a noble metal can be preferably used as a material of which the working electrodes 20 and the counter electrodes 31 are each constituted. In addition, a non-polarizable material such as silver/silver chloride can be preferably used as a material of which the reference electrodes 41 are each constituted.

Methods of forming the bases 50 of the working electrodes 20, the working electrode pads 21, the lead wires 22, the counter electrode belt 30, and the reference electrode belt 40 are not particularly limited, and arbitrary methods can be employed depending on purposes. That is, they can each be formed by, for example, a method involving the employment of photolithography using a photomask and a photoresist, and the sputtering of an electrode material.

In addition, a material having self-supporting performance by which the shape of each of the protrusion portions 51 can be maintained upon its use can be used for constituting the protrusion portions 51 without any particular limitation. For example, a synthetic resin, a photosensitive resin, or a metal material for plating can be preferably used. The synthetic resin can be particularly preferably used from the viewpoint of cost or the like.

For example, an acrylic resin such as polymethyl methacrylate or a methyl methacrylate-styrene copolymer, a styrene-based resin such as polystyrene, an olefin-based resin such as cycloolefin, an ester-based resin such as polyethylene terephthalate or polylactic acid, a silicone-based resin such as polydimethylsiloxane, or a polycarbonate resin can be used as the synthetic resin. It should be noted that any one of various additives such as a colorant, a dispersing agent, and a thickener can be incorporated into such resin as long as performance inherent in the resin is not impaired.

In addition, a method of forming the protrusion portions 51 is not particularly limited, and an arbitrary method selected depending on purposes can be employed. That is, a method such as photolithography, transfer molding using a mold, three-dimensional stereo lithography, precision machining, wet etching, dry etching, laser processing, or electric discharge machining can be employed, and at least one of those methods can be appropriately selected and employed in consideration of, for example, requested machining accuracy and cost.

In this embodiment, the protrusion portions 51 each formed of a photoresist resin cured by being irradiated with ultraviolet light through a mask are formed on the base 50 of each of the working electrodes 20 by means of photolithography. In addition, the electrode thin film 52 (see FIG. 4) formed of an electrode material is formed on the surface of each of the protrusion portions 51 by vapor deposition of gold or platinum.

In addition, at least the surface of each of the protrusion portions 51 has only to be formed of an electrode material having conductivity, and each of the protrusion portions 51 is not limited to such that the electrode thin film 52 formed of an electrode material is formed on its surface as described above. For example, the protrusion portions 51 themselves can each be constituted of an electrode material. Alternatively, for example, conductivity can be imparted to each of the protrusion portions 51 by oxidizing the protrusion portions 51 through heating after each of the protrusion portions 51 has been formed of a resin such as a photoresist resin.

In addition, for example, a resin molding method involving the use of a metal structure as a die can be employed as a method of forming the protrusion portions 51 by a transfer molding method using a mold. The resin molding method can be preferably employed because the shape of the metal structure can be reproduced in a resin-molded body at a high transfer ratio and a material cost can be reduced by using a general-purpose resin material. Such a method involving the use of the die made of the metal structure is excellent in terms of low cost and ability to satisfy high dimensional accuracy.

Plating, precision machining, wet etching, dry etching, laser processing, electric discharge machining, or the like for a resist structure produced by photolithography or for a resin structure produced by three-dimensional stereo lithography can be employed as a method of producing the metal structure, and a method appropriately selected from those methods in consideration of, for example, applications, required machining accuracy, and cost can be employed.

A method such as roll transfer based on injection molding, press molding, monomer cast molding, solvent cast molding, hot emboss molding, or extrusion molding can be employed as a method of molding the protrusion portions 51 with the metal structure produced by employing such method as a die, and a method appropriately selected from those methods in consideration of, for example, a requested shape of the structure, machining accuracy, and a cost can be employed.

In addition, a sensor substance for generating a current that can be measured with each of the working electrodes 20 by an interaction with the analyte can be immobilized on the protrusion portions 51 and base 50 of the working electrode 20. For example, a substance that is specifically bonded to the analyte can be used as the sensor substance. That is, for example, an antibody recognizing the analyte as an antigen or an enzyme recognizing the analyte as a substrate can be used.

To be specific, when an antibody is used as the sensor substance, the analyte in the solution can be immobilized on the protrusion portions 51 and base 50 of each of the working electrodes 20 through the antibody by bonding the antibody to the protrusion portions 51 and the base 50. In this case, when an antibody labeled with an enzyme is further bonded to the analyte captured by the protrusion portions 51 and the base 50, and then a substrate for the enzyme is added, a current based on a reaction between the enzyme and the substrate can be generated in the working electrode 20. Thus, a current corresponding to the amount of the analyte captured by the protrusion portions 51 and the base 50 can be measured with the working electrode 20.

It should be noted that when the analyte is a nucleic acid such as DNA or RNA, a nucleic acid probe such as a DNA probe having a base sequence that can be hybridized with the analyte can be used. In this case as well, a current based on an enzyme reaction can be measured in the same manner as in the above-mentioned example.

In addition, an electron acceptor (mediator) that mediates the exchange of electrons between the sensor substance and the electrode can also be used. In this case, a mediating layer containing the mediator such as ferrocene or benzoquinone can be formed on the surface of each of the protrusion portions 51 and the base 50.

the device 1 can be utilized as a high-sensitivity biosensor device when a biochemical interaction arises between the analyte in the solution flowing through the microchannel portion 10 and the sensor substance immobilized on the protrusion portions 51 and base 50 of each of the working electrodes 20.

Figure 5:
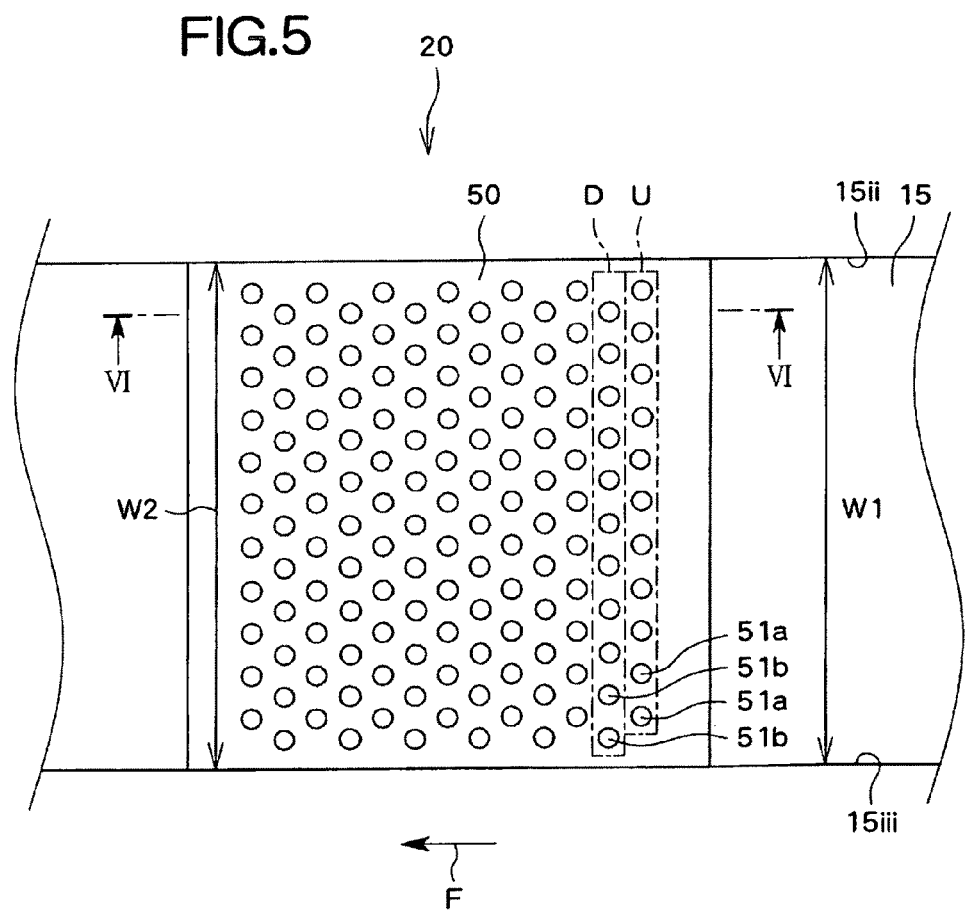
FIG. 5 is a plan view of an example of a working electrode having columnar protrusion portions according to the embodiment of the present invention.
Figure 6:
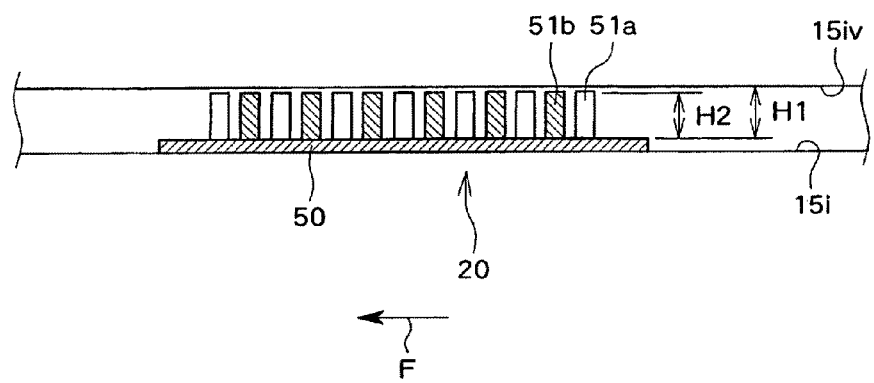
FIG. 6 is a sectional view of the electrochemical sensor device taken along the line VI-VI illustrated in FIG. 5.

FIGS. 5 and 6 each illustrate a more specific example of each of the working electrodes 20. FIG. 5 is a plan view of the working electrode 20 (view observed from the side of the channel substrate 2) and FIG. 6 is a sectional view of the working electrode 20 taken along the line VI-VI illustrated in FIG. 5. Description is given here by taking the working electrode 20 provided for the confluent portion 15 as an example. It should be noted that in the following description, the direction along the arrow F illustrated in each figure is referred to as the longitudinal direction of the confluent portion 15 and the direction perpendicular to the longitudinal direction is referred to as the width direction of the confluent portion 15.

The working electrode 20 has the planar base 50 formed along a bottom surface 15*i* of the confluent portion 15 (part of the electrode substrate 3) and the plurality of protrusion portions 51 each formed in a columnar shape protruding from the base 50.

The base 50 is formed over an entire region in the width direction of the bottom surface 15*i* of the confluent portion 15. That is, a width W2 of the base 50 is identical to a width W1 of the confluent portion 15 (distance from one side surface 15*ii* to the other side surface 15*iii*).

A height H2 of each of the protrusions 51 is slightly lower than a height H1 of the solution flowing above the base 50 (that is, a distance between the base 50 and an upper surface 15*iv* of the confluent portion 15 (part of the channel substrate 2)). It should be noted that the height H2 of each of the protrusion portions 51 can be made identical to the height H1 of the solution.

The plurality of protrusion portions 51 are regularly disposed at a constant interval. Although a distance between the adjacent protrusion portions 51 can be arbitrarily set, for example, the distance is preferably identical to or smaller than the diameter of each of the protrusion portions 51.

In addition, the protrusion portions 51 disposed so as to be adjacent to each other on an upstream side and a downstream side in the longitudinal direction of the confluent portion 15 are disposed at positions deviated from each other in the longitudinal direction. That is, for example, when attention is paid to a row surrounded by a dash-dotted line U (upstream row) and a row surrounded by a dash-dotted line D (downstream row) illustrated in FIG. 5, protrusion portions 51*b* in the downstream row are disposed on the downstream side of a gap between a pair of protrusion portions 51*a* adjacent to each other in the width direction in the upstream row.

Figure 7:
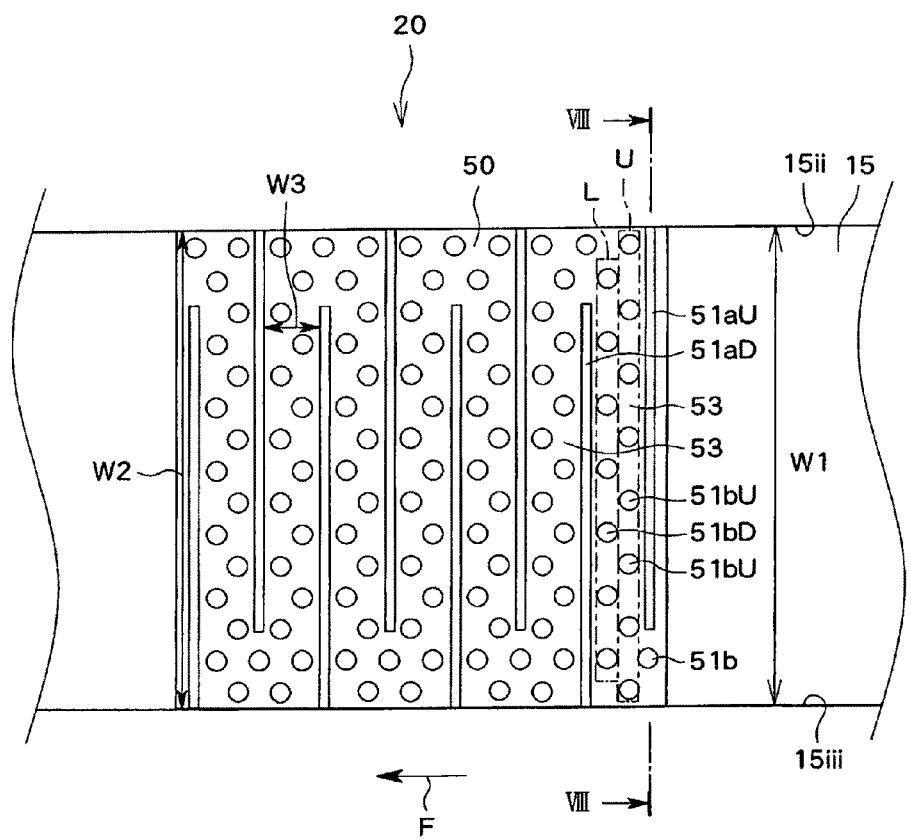
FIG. 7 is a plan view of an example of a working electrode having columnar protrusion portions and plate-like protrusion portions according to the embodiment of the present invention.
Figure 8:
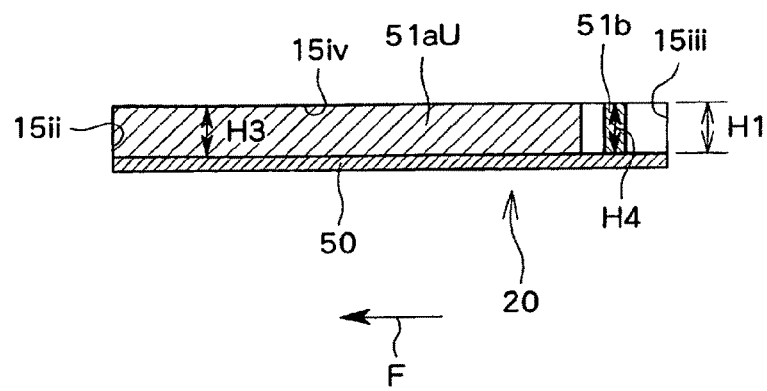
FIG. 8 is a sectional view of the electrochemical sensor device taken along the line VIII-VIII illustrated in FIG. 5.

FIGS. 7 and 8 each illustrate another example of each of the working electrodes 20. FIG. 7 is a plan view of the working electrode 20 and FIG. 8 is a sectional view of the working electrode 20 taken along the line VIII-VIII illustrated in FIG. 7.

The working electrode 20 has the planar base 50 formed along a bottom surface 15*i* of the confluent portion 15, a plurality of plate-like protrusion portions 51*a* each formed in a planar shape protruding from the base 50, and a plurality of columnar protrusion portions 51*b* each formed in a columnar shape protruding from the base 50.

As in the above-mentioned example, the width W2 of the base 50 is identical to the width W1 of the confluent portion 15. A height H3 of each of the plate-like protrusion portions 51*a* and a height H4 of each of the columnar protrusion portions 51*b* are identical to the height H1 of the solution flowing above the base 50.

The plate-like protrusion portions 51*a* extend across the confluent portion 15 so as to block part of the flow in the longitudinal direction of the confluent portion 15. That is, in this example, the plate-like protrusion portions 51*a* extend in the width direction of the confluent portion 15.

In addition, a pair of the plate-like protrusion portions 51*a* disposed so as to be adjacent and parallel to each other in the longitudinal direction of the confluent portion 15 is disposed so that the protrusion portions 51*a* may partly overlap each other in the longitudinal direction. That is, for example, part of a plate-like protrusion portion 51*a*U on the most upstream side and part of a plate-like protrusion portion 51*a*D on the downstream side of the protrusion portion 51*a*U are disposed at such positions as to overlap each other in the longitudinal direction of the confluent portion 15.

In addition, out of the pair of the plate-like protrusion portions 51*a*U and 51*a*D, the plate-like protrusion portion 51*a*U on the upstream side extends from the one side surface 15*ii* of the confluent portion 15, and the plate-like protrusion portion 51*a*D on the downstream side extends from the other side surface 15*iii* of the confluent portion 15.

As a result, a subchannel 53 extending in the width direction is formed between a pair of the plate-like protrusion portions 51*a* disposed so as to be adjacent and parallel to each other in the longitudinal direction of the confluent portion 15. That is, a gap is formed only between the plate-like protrusion portion 51*a*U on the most upstream side and the side surface 15*iii* of the confluent portion 15 out of the confluent portion 15 in the upstream end portion of the working electrode 20. On the other hand, the downstream side of the gap is blocked by the plate-like protrusion portion 51*a*D adjacent on the downstream side. In addition, a gap is formed only between the plate-like protrusion portion 51*a*D on the downstream side and the side surface 15*ii* of the confluent portion 15.

Accordingly, the solution that has flowed through the confluent portion 15 on the upstream side of the working electrode 20 flows from the gap between the plate-like protrusion portion 51*a*U on the upstream side and the side surface 15*iii* of the confluent portion 15 into the subchannel 53 formed as a space between the plate-like protrusion portion 51*a*U on the upstream side and the plate-like protrusion portion 51*a*D on the downstream side. Then, the solution flows in the width direction along the pair of the plate-like protrusion 51*a*U and

51aD, and flows out from the gap between the plate-like protrusion portion 51aD on the downstream side and the side surface 15ii of the confluent portion 15 toward the downstream side.

As described above, the pair of the plate-like protrusion portions 51aU and 51aD serves to switch the flow (main flow) in the longitudinal direction of the confluent portion 15 to the flow (subflow) in the width direction of the confluent portion 15.

In addition, a width W3 of the subchannel 53 (interval between the pair of the plate-like protrusion portions 51aU and 51aD) is smaller than the width W1 of the confluent portion 15. Accordingly, when the flow rate of the solution is kept constant, the linear velocity of the solution in the subflow increases compared to the linear velocity of the solution in the main flow. Therefore, a more turbulent flow easily occurs in the subflow than in the main flow, and hence the movement of a substance is promoted.

Further, the subchannel 53 is provided with the plurality of columnar protrusion portions 51b. In particular, in the example illustrated in FIG. 7, the protrusion portions 51b disposed so as to be adjacent to each other in the direction along the subchannel 53 (width direction of the confluent portion 15) are disposed at positions deviated from each other in the width direction. That is, for example, a columnar protrusion portion 51bD in a row on the downstream side surrounded by the dash-dotted line D is disposed in the width direction of a gap between a columnar protrusion portion 51bU in a row on the upstream side surrounded by the dash-dotted line U and the plate-like protrusion portion 51aD on the downstream side.

As a result, in the subchannel 53, the solution can flow in the width direction while efficiently contacting the columnar protrusion portions 51b. Moreover, as described above, the linear velocity in the subchannel 53 has increased. Accordingly, in the subchannel 53, the flow can be disturbed in an extremely effective fashion by the columnar protrusion portions 51b. That is, in the subchannel 53, the analyte in the solution, and the columnar protrusion portions 51b and the plate-like protrusion portions 51a, can be efficiently brought into contact with each other.

Figure 9:
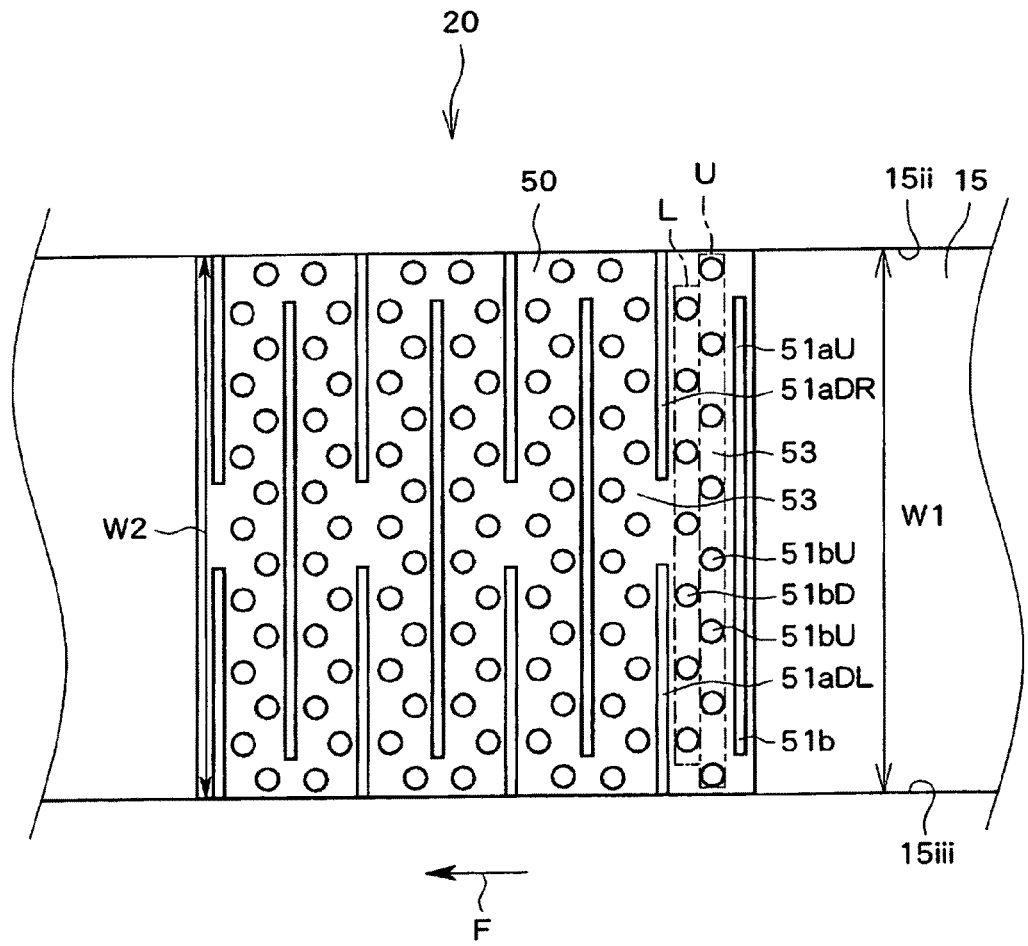
FIG. 9 is a plan view of another example of the working electrode having columnar protrusion portions and plate-like protrusion portions according to the embodiment of the present invention.

FIG. 9 is a plan view of still another example of the working electrode 20. The working electrode 20 illustrated in FIG. 9 has the planar base 50, the plurality of plate-like protrusion portions 51a, and the plurality of columnar protrusion portions 51b similar to the working electrode 20 illustrated in each of FIGS. 7 and 8.

In this example, provided between the one side surface 15ii and another side surface 15iii of the confluent portion 15 are the plate-like protrusion portions 51aU provided so that a gap may be formed between them, and plate-like protrusion portions 51aDR extending from the one side surface 15ii and plate-like protrusion portions 51aDL extending from the other side surface 15iii, the plate-like protrusion portions 51aDR and 51aDL being provided so as to be adjacent to the plate-like protrusion portions 51aU.

Therefore, the solution flowing through the confluent portion 15 flows from two gaps between the plate-like protrusion portion 51aU on the upstream side and both the side surfaces 15ii and 15iii into the subchannel 53, and flows out from one gap between the pair of the plate-like protrusion portions 51aDR and 51aDL on the downstream side toward the downstream side. In addition, in the subchannel 53, the subflow is effectively disturbed by contact with the plurality of columnar protrusion portions 51b.

Figure 10:
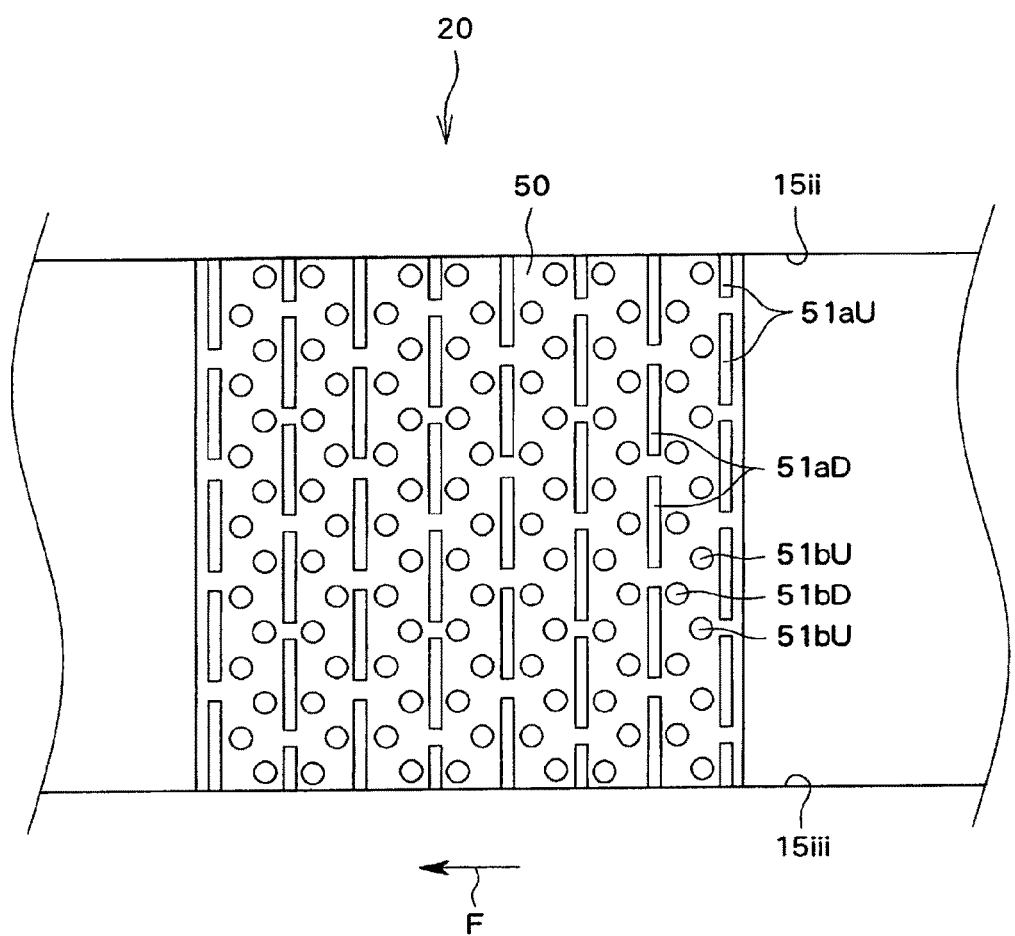
FIG. 10 is a plan view of still another example of the working electrode having columnar protrusion portions and plate-like protrusion portions according to the embodiment of the present invention.

FIG. 10 is a plan view of still another example of the working electrode 20. The working electrode 20 illustrated in FIG. 10 also has the planar base 50, the plurality of plate-like protrusion portions 51a, and the plurality of columnar protrusion portions 51b.

In this example, the plurality of plate-like protrusion portions 51a are disposed in line with each other at a predetermined interval in the width direction of the confluent portion 15. Therefore, the solution flowing through the confluent portion 15 flows from a gap between the plate-like protrusion portions 51a arranged in the width direction toward the downstream side, and efficiently contacts the plurality of columnar protrusion portions 51b in the process.

Figure 11:
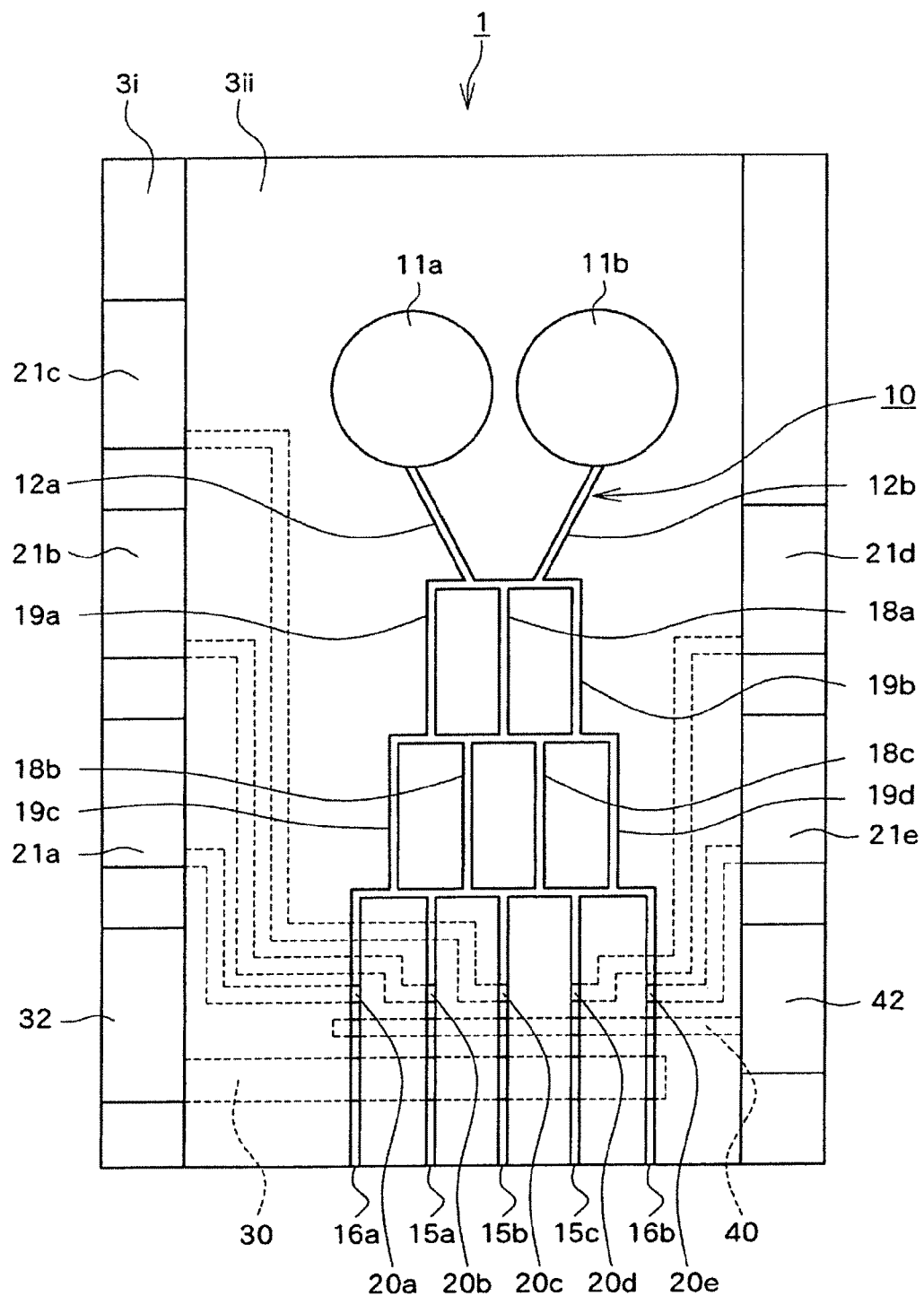
FIG. 11 is a view for describing another example of the electrochemical sensor device according to the embodiment of the present invention.

FIG. 11 illustrates a view for describing another example of the device 1. In the example illustrated in FIG. 11, the microchannel portion 10 has the two inflow portions 11a and 11b, and the two stem portions 12a and 12b as in the case of the above-mentioned example illustrated in each of FIGS. 1 to 3.

On the other hand, unlike the above-mentioned example, the microchannel portion 10 has a plurality of confluent portions 18 and 15 extending from portions where branch portions branching from the first stem portion 12a and branch portions branching from the second stem portion 12b merge with each other toward a downstream side.

In addition, the microchannel portion 10 has a plurality of first independent portions 19a, 19c, and 16a extending toward the downstream side of the first stem portion 12a without merging with any other channel, and a plurality of second independent portions 19b, 19d, and 16b extending toward the downstream side of the second stem portion 12b without merging with any other channel.

In addition, three confluent portions 15a, 15b, and 15c, and the two independent portions 16a and 16b formed as a result of the multi-stage repetition of the branching and merging of channels out of those confluent portions 18 and 15, and independent portions 19 and 16, are individually provided with the working electrodes 20.

That is, as illustrated in FIG. 11, the first independent portion 16a is provided with the first working electrode 20a, the first confluent portion 15a is provided with the second working electrode 20b, the second confluent portion 15b is provided with the third working electrode 20c, the third confluent portion 15c is provided with a fourth working electrode 20d, and the second independent portion 16b is provided with a fifth working electrode 20e. In addition, as in the case of the above-mentioned example illustrated in each of FIGS. 1 to 3, the five measuring portions 15 and 16 are provided with reference electrodes (not illustrated) as parts different from one another of the reference electrode belt individually, and are individually provided with counter electrodes (not illustrated) as parts of the counter electrode belt 30 that are different from one another. In addition, in the device 1, end portions in the width directions of the substrates 2 and 3 are provided with five working electrode pads 21a, 21b, 21c, 21d, and 21e corresponding to the five respective working electrodes 20, the one reference electrode pad 42 common to the five reference electrodes, and the one counter electrode pad 32 common to the five counter electrodes.

A first mixed solution where the first solution flowed into the first stem portion 12a and the second solution flowed into the second stem portion 12b are mixed and flow through a confluent portion 18a formed by branching and merging on a first stage. In addition, the first solution and the second solution flow as they are through the first independent portion 19a and the second independent portion 19b formed by the branching on the first stage, respectively.

A second mixed solution where the first mixed solution and the first solution are mixed, and a third mixed solution where the first mixed solution and the second solution are mixed, respectively flow through a first confluent portion 18b and a second confluent portion 18c formed by branching and merging on a second stage. In addition, the first solution and the second solution flow as they are through the first independent portion 19c and the second independent portion 19d formed by the branching on the second stage, respectively.

In addition, mixed solutions that are different from one another in composition where the first solution and the second solution are mixed at different ratios from one another flow through the three confluent portions 15a, 15b, and 15c formed by branching and merging on a third stage. That is, a fourth mixed solution, where the second mixed solution and the first solution are mixed, flows into the first confluent portion 15a, a fifth mixed solution where the second mixed solution and the third mixed solution are mixed flows into the second confluent portion 15b, and a sixth mixed solution where the third mixed solution and the second solution are mixed flows into the third confluent portion 15c. In addition, the first solution and the second solution flow as they are through the first independent portion 16a and the second independent portion 16b formed by the branching on the third stage, respectively.

Therefore, for example, when the first solution is a sample solution containing the analyte, and the second solution is a diluent solution for diluting the sample solution and is free of the analyte, the fourth mixed solution, the fifth mixed solution, and the sixth mixed solution, each of which is prepared by diluting the sample solution with the diluent solution at different dilution ratios from one another, flow through the three central confluent portions 15a, 15b, and 15c, respectively. Accordingly, in the device 1, current values corresponding to the respective concentrations of the analyte in the fourth mixed solution, the fifth mixed solution, and the sixth mixed solution, can be respectively measured with the three working electrodes 20b, 20c, and 20d formed in the three confluent portions 15a, 15b, and 15c.

In addition, the stock solution of the sample solution not diluted with the diluent solution, and the stock solution of the diluent solution not mixed with the sample solution, can be subjected to measurement with the working electrode 20a in the first independent portion 16a formed at one end of the microchannel portion 10 and the working electrode 20e in the second independent portion 16b formed at the other end of the microchannel portion 10, respectively.

As described above, the microchannel portion 10 illustrated in FIG. 11 has the independent portions 12, 19, and 16 for allowing the first solution and the second solution, which have each independently flowed into the microchannel portion 10, to flow to a downstream end as they are without mixing the solutions with any other solution, and has such a channel structure that the branching and merging of channels are repeated in stages while the number of channels disposed in parallel is increased.

Figure 12:
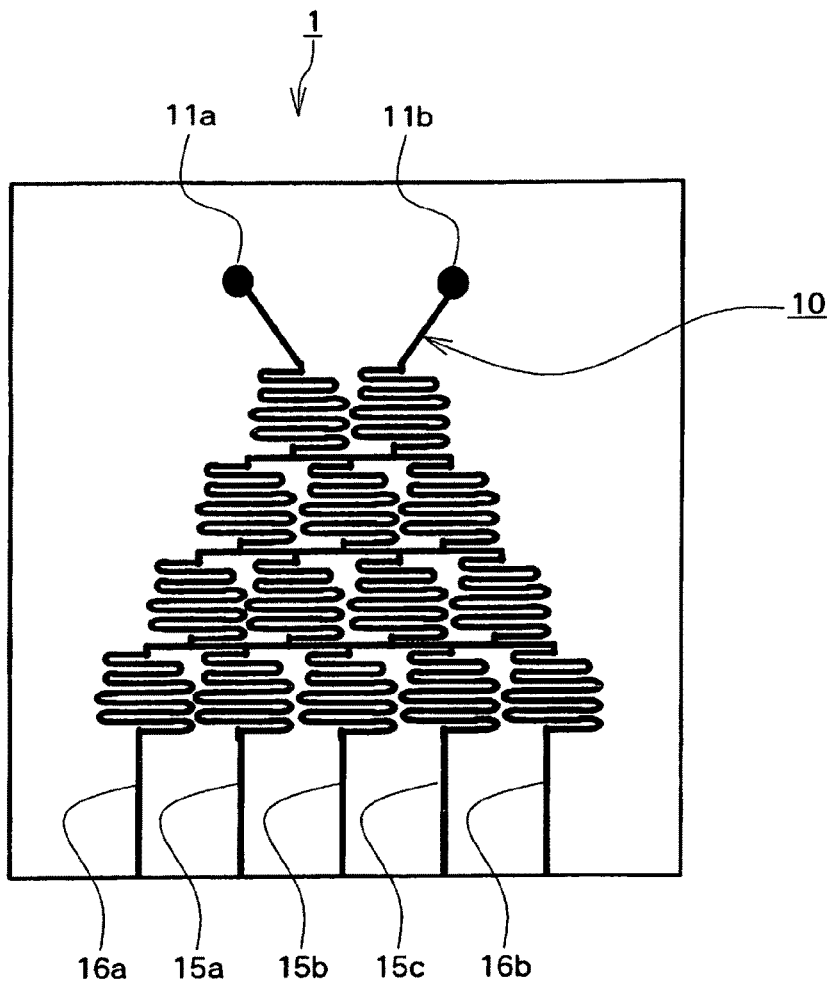
FIG. 12 is a view for describing still another example of the electrochemical sensor device according to the embodiment of the present invention.

FIG. 12 illustrates a view for describing still another example of the device 1. In the example illustrated in FIG. 12, as in the case of the example illustrated in FIG. 11, the microchannel portion 10 is of such a structure that the branching and merging of channels are repeated in a plurality of stages. In particular, however, each channel extends toward a downstream side while snaking. Because the microchannel portion 10 according to this example has snaking channels, for example, the mixing of solutions in each of the channels can be promoted.

Figure 13:
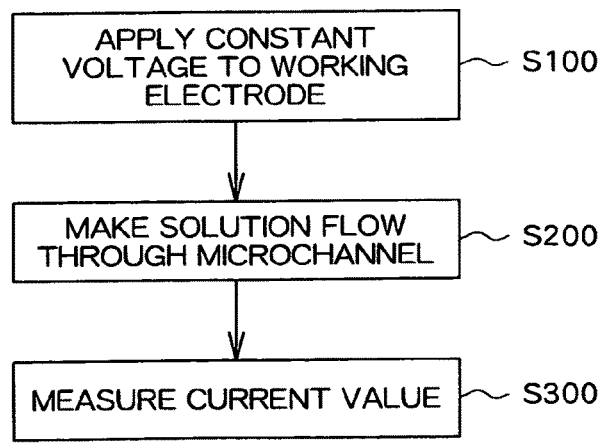
FIG. 13 is a flow chart illustrating main steps in an example of an electrochemical measuring method according to the embodiment of the present invention.

Next, the method using the device 1 is described. FIG. 13 is a flow chart illustrating main processes in an example of the method. As illustrated in FIG. 13, the method includes an applying step S100 of applying a constant voltage to each of the working electrodes 20 of the device 1, a flowing step S200 of causing a solution containing an analyte to flow through the inside of the microchannel portion 10 of the device 1, and a measuring step S300 of measuring a value for a current flowing in the working electrode 20.

In the applying step S100, for example, the microchannel portion 10 of the device 1 is filled with a predetermined solution, and the working electrode pads 21, the counter electrode pad 32, and the reference electrode pad 42 (see FIGS. 1, 3, and 11) are each connected to a voltage-applying device (such as a potentiostat) provided with an external power supply so that a constant voltage may be applied to the working electrode 20. The magnitude of the voltage applied to the working electrode 20 can be appropriately set depending on purposes. For example, a positive voltage sufficient for the oxidation of the analyte or a negative voltage sufficient for the reduction of the analyte can be applied to the working electrode 20.

In the flowing step S200, for example, the inflow tubes 4 connected to the inflow portions 11 of the microchannel portion 10 (see FIG. 1) are each connected to a pump device capable of pumping a solution at a minute flow rate (such as a microsyringe pump device), and the solution containing the analyte is made to flow into the microchannel portion 10 through each of the inflow portions 11. In this case, the solution flows in each of the measuring portions 15 and 16 of the microchannel portion 10 while weaving through the plurality of protrusion portions 51 of the working electrode 20 formed in each of the measuring portions 15 and 16. That is, when each of the protrusion portions 51 is formed in a cylindrical shape as illustrated in each of FIGS. 1, 4, 5, and 6, the solution flows while contacting the circular top surface and cylindrical side surface of each of the protrusion portions 51.

In the measuring step S300, for example, a current generated by an interaction between the analyte in the solution and the working electrode 20 in the microchannel portion 10 is measured with a current-measuring device provided for the voltage-applying device connected to the device 1. That is, for example, when a positive voltage that suffices for the oxidation of the analyte is applied to the working electrode 20 in the applying step S100, the analyte as a reductant is oxidized on the electrode surface of the working electrode 20 (the base 50 and the electrode thin film 52 of each of the protrusion portions 51 illustrated in FIG. 4). As a result, in the measuring step S300, the current flowing in the working electrode 20 in association with the oxidation of the analyte can be measured.

Thus, in the method using the device 1 illustrated in each of FIGS. 1 to 3, for example, the analyte in the solution flowing through each of the measuring portions 15 and 16 out of the microchannel portion 10 of the device can be subjected to electrochemical measurement with the working electrode 20 formed in each of the measuring portions 15 and 16.

Here, in the device 1, the working electrode 20 can perform high-sensitivity measurement because the electrode is formed so as to be of an irregular shape having the group of the protrusion portions 51 (see FIGS. 1 and 4 to 10) and its electrode surface can secure a large area as described above. That is, for example, the protrusion portions 51 of the working electrode 20 each protrude from the bottom surface 15i in each of the measuring portions 15 and 16 to extend in the channel height direction. As a result, the protrusion portions 51 can efficiently contact not only the analyte in the solution flowing near the base 50 of the working electrode 20 but also the analyte in the solution flowing at a position distant from the base 50.

As a result, according to the working electrode 20 of a concavo-convex shape provided for the device 1, even in the case where the amount of the analyte in the solution is very small, a large current value can be obtained by utilizing the large electrode surface area compared to that in the case where the working electrode 20 is formed of only the base 50.

In addition, the solution in each of the measuring portions 15 and 16 flows while colliding with the protrusion portions 51 on the base 50 of the working electrode 20, and hence the flow of the solution can be effectively disturbed on the base 50. As a result, the analyte in the solution can be efficiently brought into contact with the protrusion portions 51 and the base 50.

In particular, when the working electrode 20 has the plate-like protrusion portions 51a and the columnar protrusion portions 51b as illustrated in FIGS. 7 to 10, the solution can be made to flow through the subchannel 53 formed by the plate-like protrusion portions 51a, and the flow of the solution can be effectively disturbed by the columnar protrusion portions 51b in the subchannel 53.

In addition, when the columnar protrusion portions 51 in a row on the upstream side and the columnar protrusion portions 51 in a row on the downstream side are disposed at positions deviated from each other as illustrated in FIGS. 5 to 10, the analyte that has passed without contacting the columnar protrusion portions 51 disposed on the upstream side of the flow can be efficiently brought into contact with the columnar protrusion portions 51 on the downstream side.

Therefore, in the device 1, the microchannel portion 10 can be effectively micrified compared to a device including a conventional planar working electrode, while sufficient measurement sensitivity is maintained.

In addition, for example, in the method using the device 1 illustrated in each of FIGS. 1 to 3, the first solution and the second solution, at least one of which contains the analyte and which are different from each other in composition, are made to flow into the first stem portion 12a and the second stem portion 12b, respectively, and in the confluent portion 15, the analyte in a mixed solution prepared by the mixing of the first solution and the second solution can be subjected to electrochemical measurement with the one working electrode 20b formed in the confluent portion 15.

Similarly, for example, when the device 1 illustrated in FIG. 11 is used, the analyte in each of the three kinds of mixed solutions where the first solution and the second solution are mixed at different ratios from one another can be subjected to measurement in each of the three confluent portions 15a, 15b, and 15c.

In the device 1 including the working electrode 20 formed so as to be of a concavo-convex shape, a channel can be micrified while measurement sensitivity is maintained. Accordingly, the device 1 can include the microchannel portion 10 in which the branching and merging of channels are repeated and the mixing of solutions is favorably performed as described above. As a result, the device 1 can reliably measure a wide concentration range of the analyte.

In addition, for example, in the method using the device 1 according to the example illustrated in each of FIGS. 1 to 3, a sample solution containing the analyte is made to flow into the first stem portion 12a and a diluent solution for diluting the sample solution is made to flow into the second stem portion 12b, and in each of the first independent portion 16a and the confluent portion 15, a current value based on an interaction between the working electrode 20 and the analyte can be measured. In addition, in the second independent portion 16b, a current value based on an interaction between the working electrode 20 and the diluent solution can be measured. That is, in this case, both the solutions containing the analyte at different concentrations and the diluent solution itself are subjected to measurement with the working electrodes 20. As a result, a result of measurement for the analyte can be evaluated while a result of measurement for the diluent solution itself is defined as a reference result (blank).

In addition, similarly, for example, in the method using the device 1 illustrated in FIG. 11, in each of the first independent portion 16a, and the three confluent portions 15a, 15b, and 15c, a current value based on an interaction between the working electrode 20 and the analyte can be measured. In addition, in the second independent portion 16b, a current value based on an interaction between the working electrode 20 and the diluent solution can be measured.

In this case, the four kinds of sample solutions that are different from one another in dilution ratio can be subjected to measurement with the four working electrodes 20a, 20b, 20c, and 20d while a result of measurement for the diluent solution itself used for diluting a sample solution is acquired as a blank with the one working electrode 20e. Therefore, for example, when a biosensor device is constituted by immobilizing an antibody (sensor substance) that recognizes the analyte as an antigen on each of the working electrodes 20 of the device 1, an enzyme-linked immunosorbent assay (ELISA) that has been conventionally performed with a relatively large well plate and a diluting robot can be performed simply and swiftly. It should be noted that in this case as well, as described above, a current based on a reaction between an enzyme and a substrate for the enzyme can be measured by adding the substrate to a solution while bonding an antibody labeled with the enzyme to the analyte captured by each of the working electrodes 20.

Here, a specific example of the method by which the ELISA is performed with the device 1 is described. In this example, the device 1 is used as a chip-type biosensor device for diagnosing osteoporosis. Various proteins called bone metabolism markers (including a bone resorption marker and a bone formation marker) have been known as indicators for judging the symptom of osteoporosis. Described here is an example in which a human bone-type alkali phosphatase (BAP) known as a bone formation marker is selected as an analyte, and the quantitative determination of the BAP is performed by an ELISA using the device 1.

First, the device 1 including the plurality of confluent portions 15 illustrated in FIG. 11 is prepared. In the device 1, an anti-BAP antibody (primary antibody) is immobilized as a sensor substance on the surface (the surfaces of the base 50 and the protrusion portions 51) of the working electrode 20 provided for each of the measuring portions 15 and 16.

Next, a sample solution containing the BAP collected from a patient at an unknown concentration is made to flow from the first inflow portion 11a into the first stem portion 12a, and a diluent solution free of the BAP is made to flow from the second inflow portion 11b into the second stem portion 12b.

As a result, the linear concentration gradient of the BAP is formed in the five measuring portions 15 and 16 ranging from the first independent portion 16a to the second independent portion 16b. Then, the BAP is bonded, in an amount corresponding to the concentration in the solution that has flowed into each of the measuring portions 15 and 16, to the working electrode 20 of each of the measuring portions 15 and 16 through the anti-BAP antibody. It should be noted that, for example, in the case where liquid transport is stopped at the point in time when the first solution, the second solution, or a mixed solution of the first and second solutions reaches each of the measuring portions 15 and 16, and incubation is performed for a predetermined time period, an antigen-antibody reaction at the working electrode 20 can be reliably performed while the amount of a reagent is retrenched.

After that, a washing solution is made to flow into each of the first inflow portion 11a and the second inflow portion 11b so that the five measuring portions 15 and 16 may be sufficiently washed. The solution can be discharged from the downstream end of each of the measuring portions 15 and 16 to the outside of the device 1.

Next, a solution containing an anti-BAP antibody (secondary antibody) labeled with an enzyme (such as β-galactosidase (β-gal)) is made to flow into each of the first inflow portion 11a and the second inflow portion 11b. As a result, the enzyme-labeled anti-BAP antibody is bonded, in an amount corresponding to the amount of the BAP immobilized on the working electrode 20 of each of the measuring portions 15 and 16, to the working electrode 20. It should be noted that, in this case as well, an antigen-antibody reaction at the working electrode 20 can be reliably performed by performing incubation in a state where liquid transport is stopped as described above.

Next, a solution containing a substrate for the enzyme bonded to the secondary antibody on the working electrode 20 (such as p-aminophenyl-β-D-galactopyranoside (PAPG) as a substrate for β-gal) is made to flow into each of the first inflow portion 11a and the second inflow portion 11b. In addition, a predetermined voltage (for example, +0.7 V) is applied to each of the working electrodes 20 of the five measuring portions 15 and 16 with the voltage-applying device (such as a potentiostat) connected to the device 1.

As a result, a value for a current in association with a reaction between the substrate and the enzyme of the secondary antibody (such as a value for an oxidation current generated by the oxidation of p-imminoquinone produced by a reaction between PAPG and β-gal on the working electrode 20) can be measured with the working electrode 20. The current value is a value corresponding to the amount of the BAP immobilized on the working electrode 20, i.e., a value corresponding to the concentration of the BAP in the solution contacting each of the working electrodes 20.

Then, the concentration of the BAP in the sample solution is determined on the basis of the current value thus measured. That is, here, calibration data showing a correlation between a plurality of concentrations of the BAP and current values corresponding to the respective plurality of concentrations is prepared in a preliminary experiment. To be specific, for example, a calibration curve showing a linear relationship between a BAP concentration and a current value is acquired in advance.

Then, the concentration of the analyte in the stock solution of the sample solution is determined on the basis of current values measured for the stock solution, the diluted sample solution, and the diluent solution used for the dilution, and the calibration data. That is, for example, a concentration corresponding to a current value obtained for the working electrode 20 in the calibration data can be determined as the concentration of the BAP in the solution that has contacted the working electrode 20. When the solution is one prepared by diluting the sample solution, the concentration of the BAP in the sample solution can be determined in consideration of the dilution ratio.

Here, when a linear relationship between the concentration of the BAP and a current value is obtained only in a specific concentration range of the BAP in the calibration data, the concentration of the BAP in the solution to be brought into contact with the working electrode 20 preferably falls within the specific concentration range. In contrast, the concentration of the BAP in the sample solution collected from the patient is unknown, and may largely outstrip the above-mentioned specific concentration range in the calibration data.

Accordingly, upon performance of an ELISA, the sample solution must be diluted with the diluent solution at various ratios in stages so that solutions for measurement having various BAP concentrations may be prepared, and measurement must be conducted on each of the solutions for measurement.

However, a conventional ELISA using a pipette or dispensing robot and a multi-well plate requires a predetermined amount or more of the sample solution, and hence it has been difficult to perform the ELISA properly when the amount of the sample solution is very small.

In contrast, in the device 1, solutions for measurement having a plurality of dilution ratios in which the BAP concentration shows a desired linear relationship can be prepared simply and reliably from a trace amount of the sample solution with the microchannel portion 10. Moreover, each of the working electrodes 20 can efficiently contact the analyte in the solution because the working electrodes each have the protrusion portions 51 as described above.

As a result, the micrifying of the device 1 and high-sensitivity quantitative determination of the BAP with the device can be achieved. Therefore, the amount of the sample solution can be significantly reduced in an ELISA using the device 1 as compared to that in the conventional ELISA. In addition, the amount of a reagent used for detecting the BAP can also be significantly reduced, and hence a trace amount of the BAP substance in a trace amount of the sample solution can also be quantitated simply and reliably with a trace amount of a rare reagent.

It should be noted that, even when sample solutions having additionally various dilution ratios must be prepared, in the device 1 where the respective measuring portions 15 and 16 are individually provided with the working electrodes 20 of concavo-convex shapes, the microchannel portion 10 can be micrified while measurement sensitivity is maintained. Accordingly, for example, the device having the microchannel portion 10 capable of dilution in additionally various ways obtained by developing such a dilution channel structure as is illustrated in each of FIGS. 11 and 12 can be used.

Example 1

A flat substrate made of glass (having a diameter of 76.2 mm and a thickness of 0.05 mm) was immersed in an aqueous solution prepared by mixing 25-mass % ammonia water, 30-mass % hydrogen peroxide, and pure water at a volume ratio of 1:1:4 and boiling the mixture. The substrate was further rinsed with boiled pure water, and then air-dried.

The substrate after the drying was subjected to spin coating with a positive photoresist (S1818 manufactured by Rohm and Haas Electronic Materials LLC) under conditions of 500 rpm (5 seconds) and 2000 rpm (10 seconds). The substrate after the spin coating was baked at 80° C. for 30 minutes, and was then naturally cooled in a dark place.

Further, the substrate was irradiated with ultraviolet light for 60 seconds through a mask in which openings of shapes corresponding to a reference electrode (500 μm×2 mm), a counter electrode (500 cm×4 mm), an electrode pad (2 mm×4 mm), and a lead wire were formed with a mask aligner (manufactured by MIKASA Co., Ltd.). The substrate after the exposure was immersed in a developer (MF319 manufactured by Rohm and Haas Electronic Materials LLC), and development was performed for 1 minute. The substrate after the development was washed with distilled water, and then dried in nitrogen.

The substrate was sputtered with chromium for 5 minutes with a sputtering device (manufactured by SHIBAURA MECHATRONICS CORPORATION) at an output of 100 W under an argon atmosphere at 0.3 Pa. Next, the upper portion of the chromium layer was sputtered with platinum for 30 minutes under the same conditions. Then, the substrate was immersed in acetone (manufactured by KANTO CHEMICAL CO., INC.) for 2 hours to perform a lift-off. Thus, a counter electrode having a platinum thin film was formed on the substrate.

Next, the substrate was subjected to spin coating with a positive photoresist (S1818 manufactured by Rohm and Haas Electronic Materials LLC) under conditions of 500 rpm (5 seconds) and 2000 rpm (10 seconds). The substrate after the spin coating was baked at 80° C. for 30 minutes, and was then naturally cooled in a dark place.

Then, the substrate was irradiated with ultraviolet light for 60 seconds through a mask in which an opening of a shape corresponding to a reference electrode portion was formed with a mask aligner (manufactured by MIKASA Co., Ltd.). The substrate after the exposure was immersed in toluene at 30° C., and the mixture was stirred for 30 seconds. The substrate was baked at 80° C. for 30 minutes, and was then naturally cooled in a dark place. Further, the substrate was immersed in a developer (MF319 manufactured by Rohm and Haas Electronic Materials LLC), and development was performed for 1 minute. The substrate after the development was washed with distilled water, and then dried in nitrogen.

The substrate was sputtered with silver for 12 minutes with a sputtering device (manufactured by SHIBAURA MECHATRONICS CORPORATION) at an output of 100 W under an argon atmosphere at 0.3 Pa. Then, the substrate was immersed in acetone (manufactured by KANTO CHEMICAL CO., INC.) for 2 hours to perform a lift-off.

Next, the substrate was subjected to spin coating with polyimide (Semicofine manufactured by Toray Industries, Inc.) under conditions of 700 rpm (10 seconds) and 4000 rpm (30 seconds). The substrate after the spin coating was baked at 80° C. for 30 minutes. Further, the substrate was subjected to spin coating with a positive photoresist (S1818 manufactured by Rohm and Haas Electronic Materials LLC) under conditions of 500 rpm (5 seconds) and 2000 rpm (10 seconds). The substrate after the spin coating was baked at 80° C. for 30 minutes, and was then naturally cooled in a dark place.

Then, the substrate was irradiated with ultraviolet light for 60 seconds through a mask in which openings of shapes corresponding to the respective electrode portions, i.e., a working electrode (500 μm×500 μm), a reference electrode, and a counter electrode were formed with a mask aligner (manufactured by MIKASA Co., Ltd.). The substrate after the exposure was immersed in 99.5% ethanol (manufactured by KANTO CHEMICAL CO., INC.) for 5 minutes to remove unnecessary polyimide. The operation was repeated twice. The substrate was sequentially baked at 150° C. for 15 minutes, then at 200° C. for 15 minutes, and further, at 300° C. for 30 minutes to cure polyimide on the substrate. Thus, an insulating film was formed.

The substrate was immersed in a 1.0-M KCl—HCl buffer (having a pH of 2.2) at 25° C. in a predetermined container. Further, a silver/silver chloride reference electrode (manufactured by HORIBA, Ltd.) and a platinum counter electrode were immersed in the container, and the reference electrode portion of the substrate, and the reference electrode and the platinum counter electrode were connected to a galvanostat (manufactured by HOKUTO DENKO CORPORATION). Then, a current of 0.1 μA was applied for 5 minutes to form silver chloride in the reference electrode portion. After that, the substrate was washed with distilled water, and then air-dried. Thus, a reference electrode having a silver/silver chloride thin film was formed on the substrate.

Next, the upper portion of the substrate was subjected to spin coating with a negative photoresist (SU-8-25 manufactured by Kayaku MicroChem) under conditions of 500 rpm (10 seconds) and 800 rpm (30 seconds). The substrate after the spin coating was baked with a hot plate at 65° C. for 5 minutes, and further, was baked with a hot plate at 95° C. for 15 minutes. After that, the substrate was naturally cooled in a dark place.

Then, the substrate in the range corresponding to the working electrode portion was irradiated with ultraviolet light for 180 seconds through a mask in which circular openings each having a diameter of 20 μm were formed in such a regular arrangement that a distance between the centers of the circles was 40 μm with a mask aligner (manufactured by MIKASA Co., Ltd.). The substrate after the exposure was baked with a hot plate at 65° C. for 1 minute, and was further baked with a hot plate at 95° C. for 4 minutes. Then, the substrate was immersed in a developer (SU-8 Developer manufactured by Kayaku MicroChem), and development was performed for 5 minutes. The substrate after the development was dried in nitrogen. Thus, 143 cylindrical protrusions (pillars) each having a diameter of 20 μm and a height of 50 μm were formed in the range of the working electrode portion.

The substrate was cut into a rectangle measuring 15 mm by 20 mm with a dicing saw (manufactured by TOKYO SEIMITSU CO., LTD.). The substrate after the cutting was washed with pure water and air-dried. Further, a metal mask in which an opening of a shape corresponding to the working electrode portion was formed was fixed to the substrate with a polyimide tape. After that, the resultant was sputtered with chromium for 5 minutes with a sputtering device (manufactured by SHIBAURA MECHATRONICS CORPORATION) at an output of 100 W under an argon atmosphere at 0.3 Pa. Next, the upper portion of the chromium layer was sputtered with platinum for 30 minutes under the same conditions. Thus, a working electrode having a platinum electrode surface including a plurality of pillar surfaces was formed.

Figure 14:
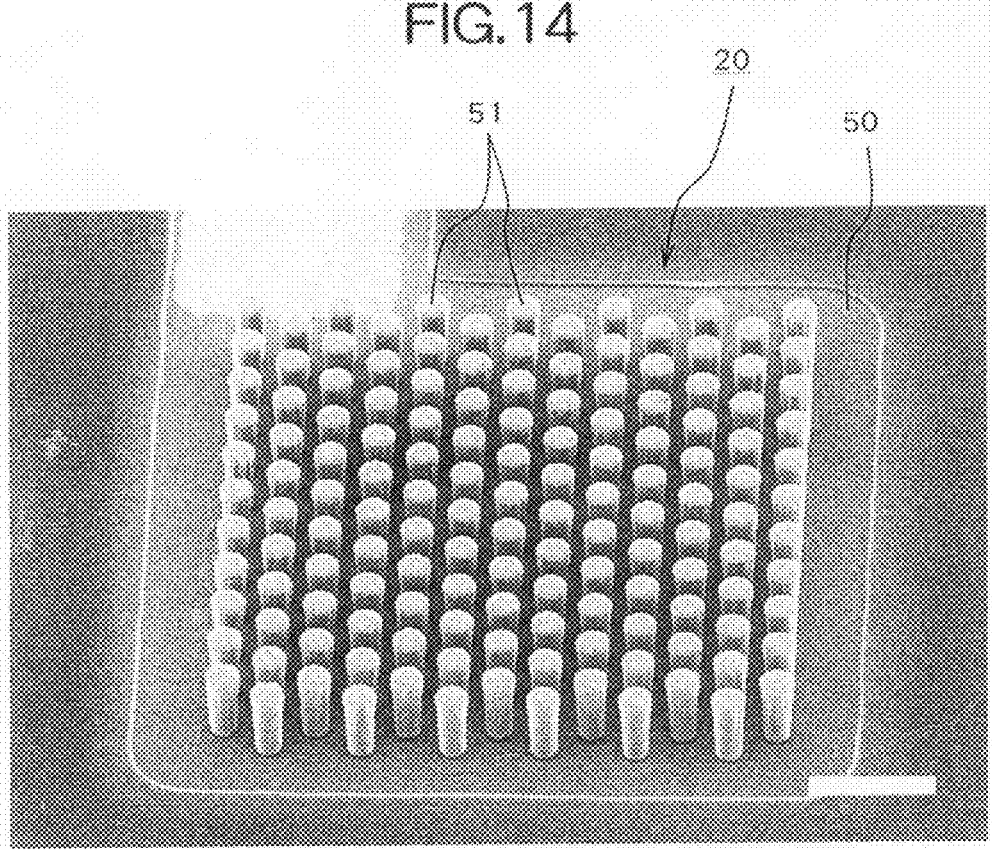
FIG. 14 is an electron micrograph of the example of the working electrode according to the embodiment of the present invention.

FIG. 14 illustrates an electron micrograph of the working electrode 20 thus produced. As illustrated in FIG. 14, the working electrode 20 had the base 50 and a plurality of cylindrical pillars 51 formed on the base 50 so as to protrude, each having a platinum thin film formed on its surface. It should be noted that the length of a white line illustrated in FIG. 14 represents 100 μm.

Figure 15:
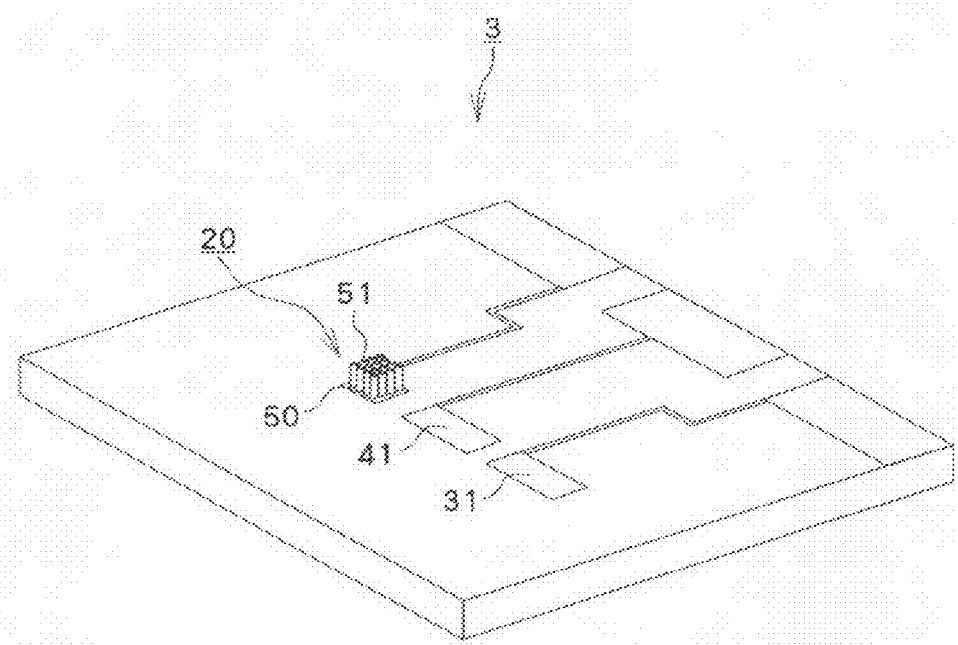
FIG. 15 is a view for describing another example of the electrode substrate according to the embodiment of the present invention.

Thus, as illustrated in FIG. 15, the electrode substrate 3 including the platinum working electrode 20 having the plurality of pillars 51, the silver/silver chloride reference electrode 41, and the platinum counter electrode 31 was produced.

Example 2

The working electrode 20, silver/silver chloride reference electrode 41 (manufactured by HORIBA, Ltd.), and platinum counter electrode 31 of the electrode substrate 3 produced as described above were immersed in a phosphate buffer (having a pH of 7.4) containing 0.1-M $KH_3PO_4$ and 0.1-M KCl in a predetermined container. Then, the working electrode 20, silver/silver chloride reference electrode 41, and platinum counter electrode 31 of the electrode substrate 3 were each connected to a potentiostat (manufactured by HOKUTO DENKO CORPORATION). Then, 200 μL of a 100-mM $H_2O_2$ solution were dropped into the phosphate buffer while a steady voltage of +0.7 V was applied, and a current value at the time of the dropping was measured. Additional dropping of the $H_2O_2$ solution and the measurement of a current value after the dropping were similarly repeated several times.

In addition, a control substrate having a working electrode (500 μm×500 μm) on which the pillars 51 were not formed (i.e., the base 50 alone) was produced in the same manner as in the above-mentioned method of producing the electrode substrate 3. Then, the dropping of the $H_2O_2$ solution and the measurement of a current value after the dropping were performed by using the control substrate in the same manner as in the case of the electrode substrate described above.

Figure 16:
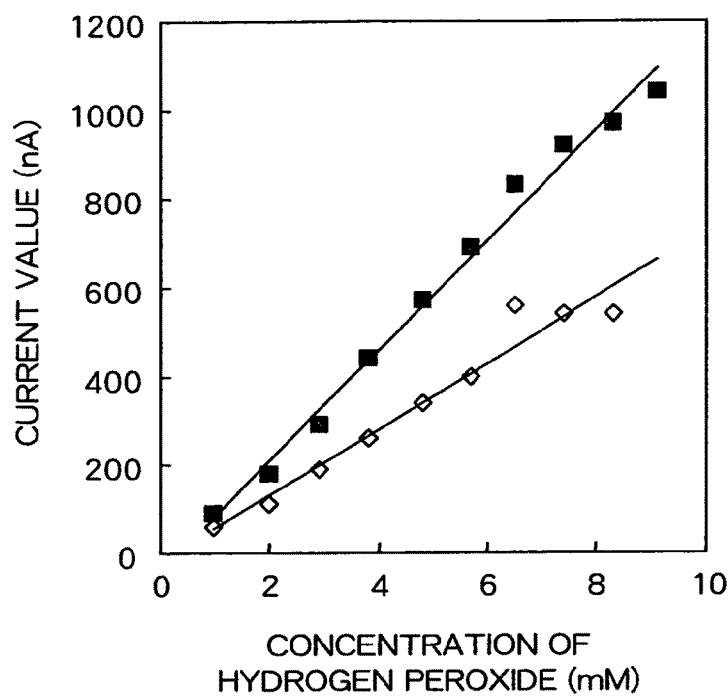
FIG. 16 is a view for describing an example of results of the measurement of a current value in the embodiment of the present invention.

FIG. 16 illustrates a relationship between the concentration of $H_2O_2$ in the phosphate buffer corresponding to the amount in which the $H_2O_2$ solution was dropped and a current value measured at each $H_2O_2$ concentration. In FIG. 16, the axis of abscissa indicates the concentration of $H_2O_2$ (mM) and the axis of ordinate indicates a measured current value (nA). In addition, square marks represent the results of the measurement with the electrode substrate 3 and diamond marks represent the results of the measurement with the control substrate. As illustrated in FIG. 16, at the same $H_2O_2$ concentration, a current value obtained in the electrode substrate 3 was 1.5 to 1.8 times as large as that obtained in the control substrate.

Example 3

The upper portion of a flat substrate made of glass, and washed with an aqueous solution prepared by mixing 25-mass % ammonia water, 30-mass % hydrogen peroxide, and pure water at a volume ratio of 1:1:4 and boiling the mixture, was subjected to spin coating with a negative photoresist (SU-8-25 manufactured by Kayaku MicroChem) under conditions of 500 rpm (10 seconds) and 750 rpm (30 seconds). The substrate after the spin coating was baked with a hot plate at 65° C. for 5 minutes, and further, was baked with a hot plate at 95° C. for 15 minutes. After that, the substrate was naturally cooled in a dark place.

Further, the substrate was irradiated with ultraviolet light for 120 seconds through a mask in which an opening of a shape corresponding to one linear microchannel portion (0.5 mm×16.5 mm) including the working electrode 20, the reference electrode 41, and the counter electrode 31 illustrated in FIG. 15 was formed with a mask aligner (manufactured by MIKASA Co., Ltd.). The substrate after the exposure was baked with a hot plate at 65° C. for 1 minute, and further, was baked with a hot plate at 95° C. for 4 minutes. Then, the substrate was immersed in a developer (SU-8 Developer manufactured by Kayaku MicroChem), and development was performed for 5 minutes. The substrate after the development was dried in nitrogen.

Then, the substrate after the drying was mounted in a predetermined container, and a reaction liquid prepared by mixing a precursor for polydimethylsiloxane (PDMS, manufactured by Shin-Etsu Chemical Co., Ltd.) and a curing agent at a mass ratio of 10:1 was poured into the container. The container was disposed in a desiccator, and the reaction liquid was defoamed with a vacuum pump. The reaction liquid was cured by being left to stand at room temperature for 24 hours, and the cured PDMS-molded body was peeled from the substrate. Thus, the channel substrate 2 made of PDMS in which the one linear microchannel portion 10 (0.5 mm×16.5 mm) was formed was produced.

Further, a through-hole having a diameter of 2 mm, into which a solution will be made to flow, was formed in the channel substrate 2 at the upstream end portion of the microchannel portion 10. Then, the channel substrate 2 was superimposed on the electrode substrate 3 produced as described above. Thus, the device 1 was constituted.

One end of a silicone tube (manufactured by AS ONE Corporation) having an inner diameter of 0.5 mm and an outer diameter of 1 mm was connected to the through-hole formed in the channel substrate 2 of the device 1, and fixed with an adhesive (one-component RTV rubber manufactured by Shin-Etsu Chemical Co., Ltd.). A microsyringe (1 mL, manufactured by Bioanalytical Systems, Inc.) was connected to the other end of the silicone tube, and the microsyringe was installed in a microsyringe pump (manufactured by Bioanalytical Systems, Inc.). In addition, the working electrode 20, reference electrode 41, and counter electrode 31 of the device 1 were each connected to a potentiostat (manufactured by HOKUTO DENKO CORPORATION).

Then, a 0.2-mM aqueous solution of $H_2O_2$ was made to flow through the microchannel portion 10 in the device 1 at a flow velocity of 10 μL/min. At the same time, a constant potential of +0.7 V (with respect to the silver/silver chloride reference electrode) was applied to the working electrode 20 of the device 1 with a potentiostat, and a value for a current generated in association with the flow of the aqueous solution of $H_2O_2$ was recorded with the recorder of the potentiostat.

In addition, a control device was produced by superimposing the channel substrate 2 produced as described above on the control substrate having a working electrode (500 μm×500 μm) on which the pillars 51 were not formed in the same manner as in the above-mentioned method of producing the device 1. Then, a current value at the time of the flow of the $H_2O_2$ solution was measured with the control device as in the case of the device 1 described above.

Figure 17:
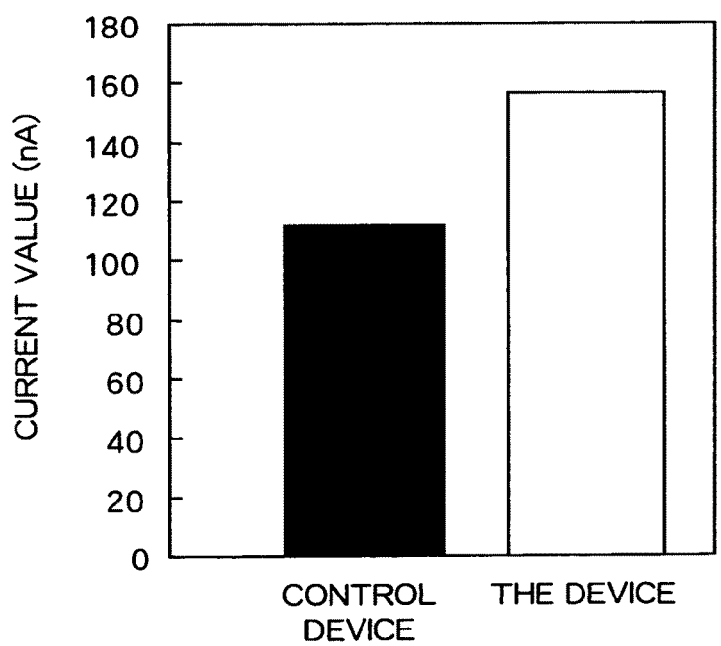
FIG. 17 is a view for describing another example of the results of the measurement of a current value in the embodiment of the present invention.

FIG. 17 illustrates the results of the measurement for the current values thus measured. In FIG. 17, a void bar indicates the current value (nA) measured with the device 1 and a solid bar indicates the current value (nA) measured with the control device. As illustrated in FIG. 17, a current value obtained in the device 1 was about 1.6 times as large as that obtained in the control device. In other words, it was confirmed that, in the device 1, for example, additional micromachining of the microchannel portion was attained compared to the control device, while measurement sensitivity was maintained at the same level as that of the control device.

The measurement of a current value with the device 1 actually produced and a simulation with a computer were performed in order to identify an effect of the protrusion portions 51 in the device 1.

Example 4

FIG. 18 illustrates comparison among conditions for four kinds of the working electrodes 20 adopted here. In other words, here, a flat working electrode (flat) formed only of the base 50 and free of the protrusion portions 51, a working electrode (φ30) having the cylindrical protrusion portions (pillars) 51 each having a diameter of 30 μm, a working electrode (φ20) having the cylindrical pillars 51 each having a diameter of 20 μm, and a working electrode (φ10) having the cylindrical pillars 51 each having a diameter of 10 μm were objects of investigation.

It should be noted that in each of the four kinds of the working electrodes 20, the base 50 was formed as a rectangular, conductive thin film (500 μm×500 μm), and the pillars 51 were regularly disposed on the base 50 at an interval and a number illustrated in FIG. 18, as illustrated in FIG. 5. In addition, the height H2 of each of the pillars 51 was 50 μm and the height H1 of the microchannel portion 10 was 55 μm (see FIG. 6).

Then, as in the case of Example 3 described above, a sensor device having one of the above-mentioned four kinds as the working electrode 20 was produced. Ascorbic acid was used as an analyte. When ascorbic acid contacts the conductive surface of the working electrode 20 to which a voltage has been applied, a current in association with the oxidation of ascorbic acid flows in the working electrode 20.

In view of the foregoing, a phosphate buffer (having a pH of 7.4) containing ascorbic acid at a concentration of 1 mM was made to flow through the microchannel portion 10 of each sensor device at a flow velocity of 10 μL/min. At the same time, a constant potential (+0.7 V) with respect to the silver/silver chloride reference electrode was applied to the working electrode 20 of each sensor device with a potentiostat. Then, in each sensor device, a value for a current generated in association with the flow of the solution containing ascorbic acid was measured with the working electrode 20, and was recorded with the recorder of the potentiostat.

Meanwhile, a simulation was performed by a finite difference method using an equation for concentration transport diffusion represented by the following equation (I). A general-purpose flow analysis code (FLOW3D, Flow Science Inc.) was used in numerical calculation with a computer.

[Num 1]

$$\frac{\partial c}{\partial t} + \nabla \cdot CU = D\nabla^2 U - D_s AC \quad (I)$$

In the equation (I), C represents a molar concentration per unit volume (mol/cm$^3$), A represents a surface area (cm$^2$), U represents a flow velocity (cm/s), D represents a diffusion coefficient (cm$^2$/s), and Ds represents a concentration consumption volume velocity per unit area (cm$^3$/cm$^2$·s).

The amount of ascorbic acid flowing into a channel inlet (the upstream end of the working electrode 20) per unit time (mol/s) was calculated as the product of the concentration (mol/cm$^3$) and flow rate (cm$^3$/s) of ascorbic acid at the channel inlet.

In addition, the amount of ascorbic acid moving in a certain minute element on a section of a channel outlet (the downstream end of the working electrode 20) per unit time (mol/s) was calculated as the product of a concentration (mol/cm$^3$) and a flow rate (cm$^3$/s) for the minute element. Similar calculation was conducted on all minute elements on the section of the outlet, and the amount of ascorbic acid flowing out of the channel outlet per unit time (mol/s) was calculated by summing the results.

Then, the amount of ascorbic acid reacting in the channel per unit time (reacting weight of ascorbic acid per unit time) (mol/s) was calculated as a difference between the inflow amount (mol/s) and the outflow amount (mol/s) described above.

It should be noted that the concentration consumption volume velocity Ds used in the simulation was determined on the basis of an actual result of measurement. In other words, first, numerical simulation analysis was conducted on the microchannel portion 10 on which the flat working electrode 20 formed of only the base 50 was disposed with a certain value for Ds, and the reacting weight per unit time (mol/s) of ascorbic acid was calculated.

Meanwhile, a sensor device provided with the flat working electrode 20 similar to that in the simulation was actually produced, and a value for an oxidation current (A) when a solution of ascorbic acid was made to flow in the sensor device under conditions identical to those of the above-mentioned simulation was measured.

Then, the reacting weight per unit time (mol/s) of ascorbic acid was calculated from the measured current value by using the following equation (II).

[Num 2]

$$\Delta C = \frac{\Delta I}{a \cdot F \cdot Q} \quad (II)$$

In the equation, C represents the concentration (mol/L) of ascorbic acid, a represents the number of electrons generated by the oxidation reaction of one mole of ascorbic acid, F represents the Faraday constant (C/mol), Q represents a flow rate (L/s), and I represents the measured current value (A).

The simulation result and the measured result thus obtained were compared, and a value for Ds was determined so that those results would coincide with each other. As a result, Ds was determined to be 0.00072 cm$^3$/cm$^2$·s.

FIG. 19 illustrates the results of the current values (μA) obtained for the four kinds of the working electrodes 20 in correspondence with the electrode surface areas (mm$^2$) of the electrodes. In FIG. 19, solid circle marks represent the current values actually measured with the sensor devices and void circle marks represent the current values calculated by the simulation.

As illustrated in FIG. 19, a current value to be measured increased with increasing surface area of the working electrode 20. In other words, the measurement sensitivity of the working electrode 20 having the pillars 51 was higher than that of the working electrode free of the pillars 51.

In addition, the simulation results coincided well with the results actually measured with the sensor devices. In other words, it was confirmed that the simulation was useful in accurately forecasting a flow in the microchannel portion 10 based on the structure of the working electrode 20.

FIG. 20 illustrates results calculated by the simulation of an ascorbic acid concentration distribution in the microchannel portion 10 in a side view where the microchannel portion 10 is cut along the direction in which the pillars 51 extend.

In FIG. 20, the concentration of ascorbic acid is visually represented with gradation from black to white. The darker and closer to black a color is, the higher the concentration of ascorbic acid. Therefore, the lighter and closer to white a color is, the larger the amount (reacting weight) of ascorbic acid that has disappeared owing to a reaction at the surface of the working electrode 20.

As illustrated in FIG. 20, it can be found that, in the microchannel portion 10 provided with the flat working electrode 20 free of the pillars 51 (the uppermost result of FIG. 20), the concentration of ascorbic acid is reduced by a reaction with the working electrode 20 in the vicinity of the working electrode 20 (that is, the base 50) (that is, the vicinity of the bottom surface of the microchannel portion 10), but ascorbic acid passes over without reacting with the working electrode 20 at a position distant from the working electrode 20.

In contrast, it can be found that when the working electrode 20 has the pillars, the concentration of ascorbic acid reduces not only in the vicinity of the bottom surface of the microchannel portion 10 but also at a position distant from the bottom surface. The foregoing means that the conductive pillars 51 each protruding toward a position distant from the bottom surface of the microchannel portion 10 (upper side in the height direction of the microchannel portion 10) allow ascorbic acid in the solution flowing through the microchannel portion 10 to react with the surfaces of the pillars 51 efficiently. In particular, it was confirmed that, as the diameter of each of the pillars 51 was reduced and the number of the pillars increased, it was possible to cause ascorbic acid in the solution flowing above the working electrode 20 to react with the working electrode 20 in a larger amount with higher accuracy.

In addition, FIG. 21 each illustrate the concentration distribution of ascorbic acid at a position distant from the bottom surface of the microchannel portion 10 provided with the flat working electrode 20 or of the microchannel portion 10 provided with the pillars 51 each having a diameter of 20 μm by 27.5 μm. It should be noted that in each of the microchannel portions 10, the solution was assumed to flow from the right side toward the left side in each figure. In addition, in each of FIG. 21, the axis of abscissa indicates a position (x coordinate) in the longitudinal direction of the microchannel portion 10 and the axis of ordinate indicates a position (y coordinate) in the width direction of the microchannel portion 10. Here, analysis was conducted in a range measuring 110 μm in the longitudinal direction by 50 μm in the width direction of each of the microchannel portions 10.

As can be seen from FIG. 21A, when the microchannel portion has the flat working electrode 20, the solution passes above the working electrode 20 while maintaining a high ascorbic acid concentration. In addition, FIG. 21B corroborated that when the working electrode 20 had the pillars 51, causing the surface of the working electrode 20 and ascorbic acid to react with each other made it possible to reduce the concentration of ascorbic acid effectively.

In view of the foregoing, next, a simulation was similarly conducted on the working electrode 20 having the plate-like protrusion portions 51a and the columnar protrusion portions 51b illustrated in each of FIGS. 7 to 10. The pillars 51b each had a diameter of 20 μm, the plate-like protrusion portions 51a each had a thickness (length in the longitudinal direction of the microchannel portion 10) of 10 μm, the pillars 51b and the plate-like protrusion portions 51a each had a height of 50 μm, and the microchannel portion 10 had a height of 50 μm.

In addition, for comparison, a simulation was similarly conducted on the working electrode 20 having the plate-like protrusion portions 51a and the base 50 as illustrated in FIG. 7 and free of the columnar protrusion portions 51b.

FIGS. 22 and 23 illustrate the concentration distributions of ascorbic acid in the respective microchannel portions 10 similar to FIG. 21. It should be noted that, in each of FIGS. 22 and 23, a portion represented with a white color was considered to be not a region where ascorbic acid was consumed and hence its concentration reduced, but a region through which the solution containing ascorbic acid did not flow.

Figure 24:
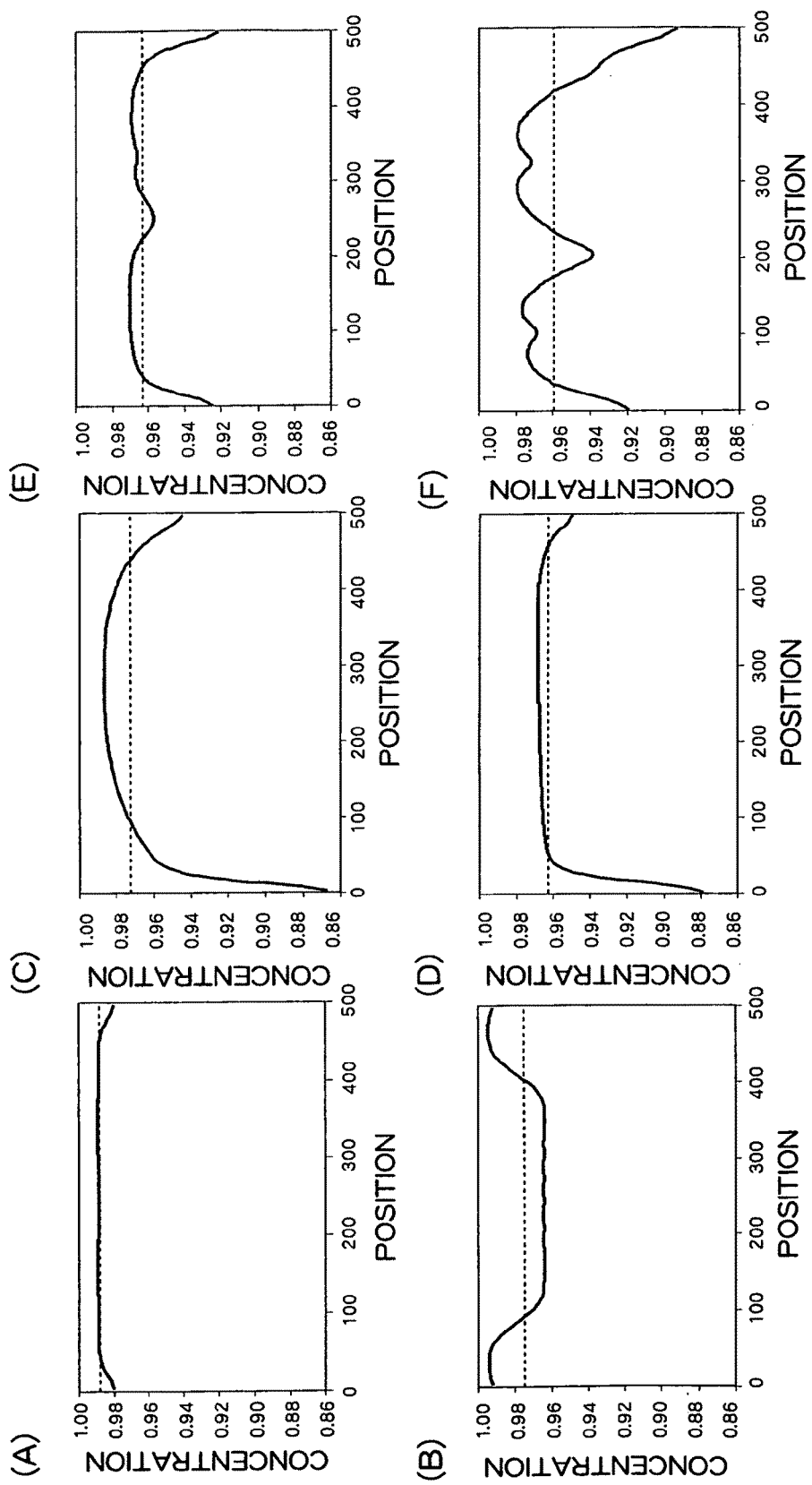
FIG. 24 are each a view for describing an example of a concentration distribution in a channel width direction obtained in the simulation of the embodiment of the present invention.

In addition, FIG. 24 illustrate concentration distributions in the width directions of the six kinds of microchannel portions 10 illustrated in FIGS. 21, 22, and 23 at the downstream ends of the microchannel portions 10. FIGS. 24A and 24B correspond to FIGS. 21A and 21B, respectively, FIGS. 24C and 24D correspond to FIGS. 22A and 22B, respectively, and FIGS. 24E and 24F correspond to FIGS. 23A and 23B, respectively. In each of FIG. 24, the axis of abscissa indicates a position (μm) in the width direction of the microchannel portion 10, the axis of ordinate indicates the concentration (mM) of ascorbic acid, a solid line indicates a concentration distribution in the result of the simulation, and a broken line indicates the level of an average concentration.

Figure 25:
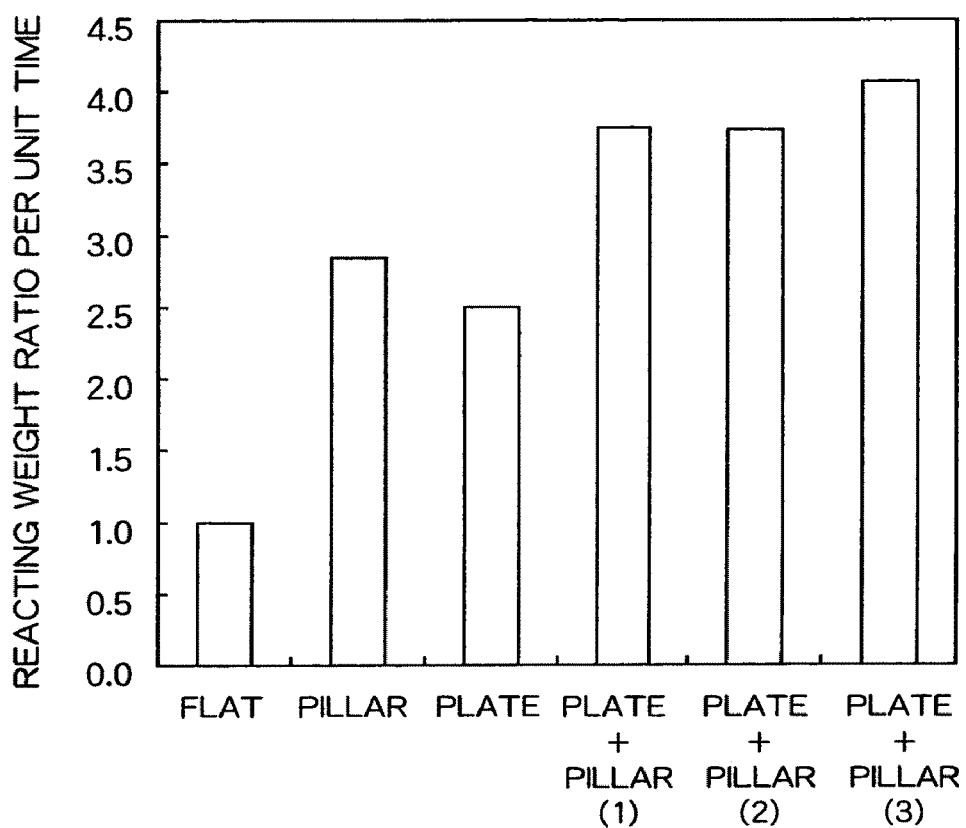
FIG. 25 is a view for describing an example of a reacting weight ratio obtained in the simulations of the embodiment of the present invention.

Further, FIG. 25 illustrates reacting weight ratios per unit time of ascorbic acid calculated as described above for the above-mentioned six kinds of microchannel portions 10. In FIG. 25, the axis of abscissa indicates the kind of the working electrode 20 and the axis of ordinate indicates a ratio of a reacting weight under each condition to the reacting weight in the flat working electrode 20 free of the protrusions 51.

On the axis of abscissa of FIG. 25, the terms "FLAT" and "PILLAR" correspond to the working electrodes 20 of FIGS. 21A and 21B, respectively, the terms "PLATE" and "PLATE+PILLAR (1)" correspond to the working electrodes 20 of FIGS. 22A and 22B, respectively, and the terms "PLATE+PILLAR (2)" and "PLATE+PILLAR (3)" correspond to the working electrodes 20 of FIGS. 23A and 23B, respectively.

FIGS. 24 and 25 confirmed that, in the case where the working electrode 20 had the pillars 51b or the plate-like protrusion portions 51a, the reacting weight of ascorbic acid significantly increased and the concentration of ascorbic acid in the solution flowing out of the working electrode 20 was reduced compared to those in the case where the working electrode was free of those protrusion portions 51.

Further it was also confirmed that in the case where the working electrode 20 had both of the pillars 51b and the plate-like protrusion portions 51a, the reacting weight of ascorbic acid further increased compared to that in the case where the working electrode only had any one of the pillars 51b and the plate-like protrusion portions 51a.

Figure 26:
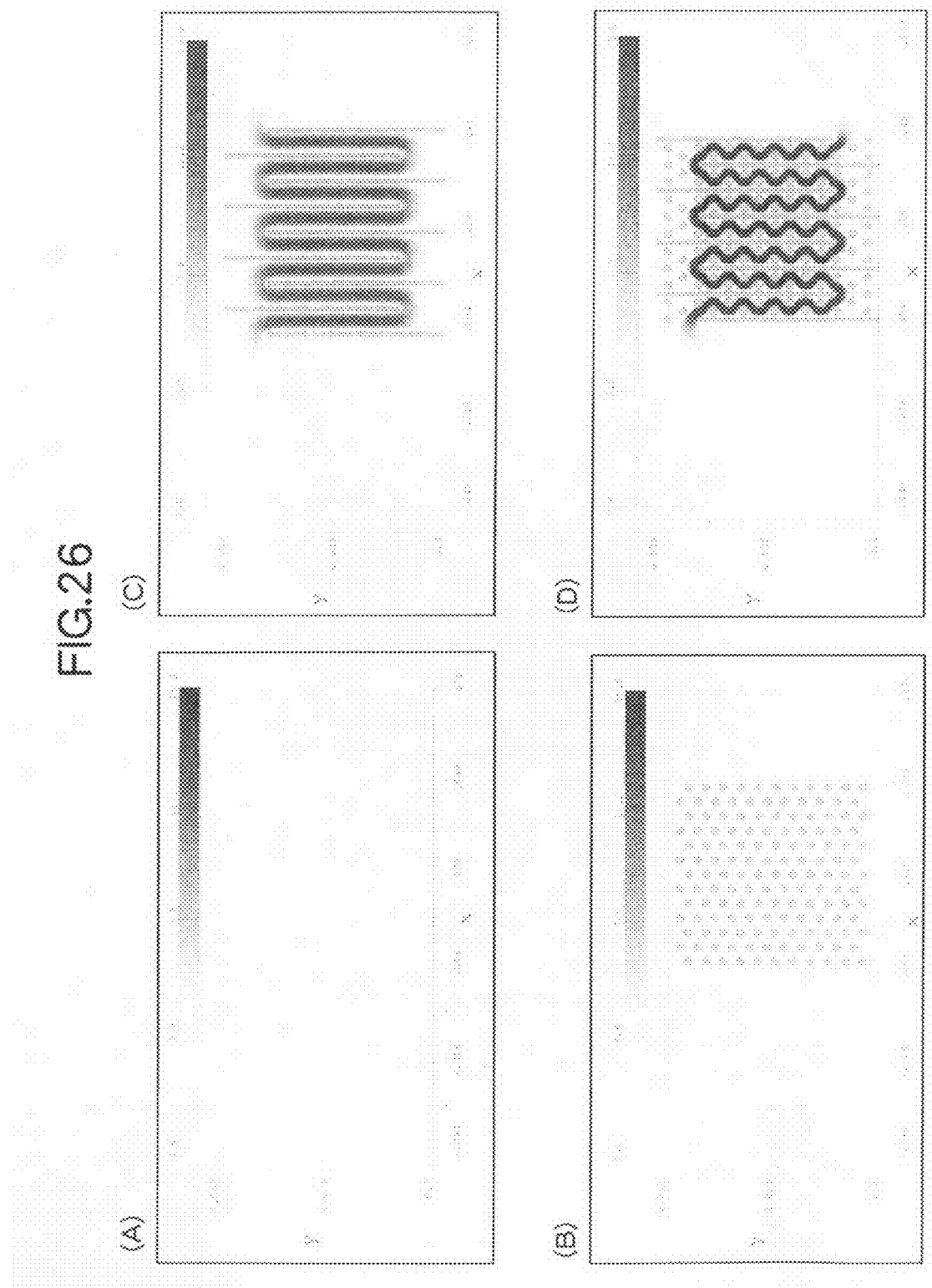
FIG. 26 are each a view for describing an example of a velocity vector distribution obtained in the simulation of the embodiment of the present invention.

FIG. 26 illustrate part of results corroborating an effect of disposing the pillars 51b between the plate-like protrusion portions 51a. FIG. 26 illustrate local velocity vector distributions at the same positions as the positions at which the four kinds of microchannel portions 10 illustrated in FIGS. 21 and 22 were evaluated for their concentration distributions. In each of FIG. 26, the darker and closer to black a color is, the larger a velocity vector.

No particular region where the velocity vector was locally large was observed in either of the working electrode 20 formed of only the base 50 (FIG. 26A) and the working electrode 20 formed of the base 50 and the pillars 51b (FIG. 26B).

In contrast, as illustrated in FIG. 26C, when the plate-like protrusion portions 51a crossing the microchannel portion 10 were provided, a region where the velocity vector significantly increased was observed between the plate-like protrusion portions 51a.

Further, as illustrated in FIG. 26D, in the case where the pillars 51b were disposed between the plate-like protrusion portions 51a, the velocity vector further increased compared to that in the case where only the plate-like protrusion portions 51a were provided (FIG. 26C).

In other words, when the plate-like protrusion portions 51a were provided first before the subchannels 53 (see FIG. 7) were formed, a significant increase of the velocity vector in each of the subchannels 53 was attained.

In this case, as illustrated in FIG. 26D, further providing the subchannel 53 with the pillars 51b is expected to show a situation where a rapid flow in the subchannel 53 collides with the pillars 51b, to thus be effectively disturbed.

As a result, in the subchannel 53, it is considered to be possible to efficiently bring ascorbic acid in the solution passing between the pillars 51b or between the pillars 51b and the plate-like protrusion portions 51a into contact with the electrode surface of each of the pillars 51b and the plate-like protrusion portions 51a.

In addition, in the working electrode 20 illustrated in FIG. 26D, the entirety of the solution flowing from the upstream side into the working electrode 20 can be reliably introduced into the subchannel 53 from one inlet, and can be efficiently brought into contact with the pillars 51b in the subchannel 53.

A similar effect can be obtained in, for example, the working electrode 20 illustrated in FIG. 23A as well. That is, in the working electrode 20, inlets to the subchannel 53 on the most upstream side exist at two sites, but the outlet of a flow from the subchannel 53 to the subchannel 53 on the downstream side exists at only one site, i.e., a center in the width direction of the microchannel portion 10. As a result, the entirety of the solution flowing into the working electrode 20 can be reliably introduced into the subchannel 53.

Figure 27:
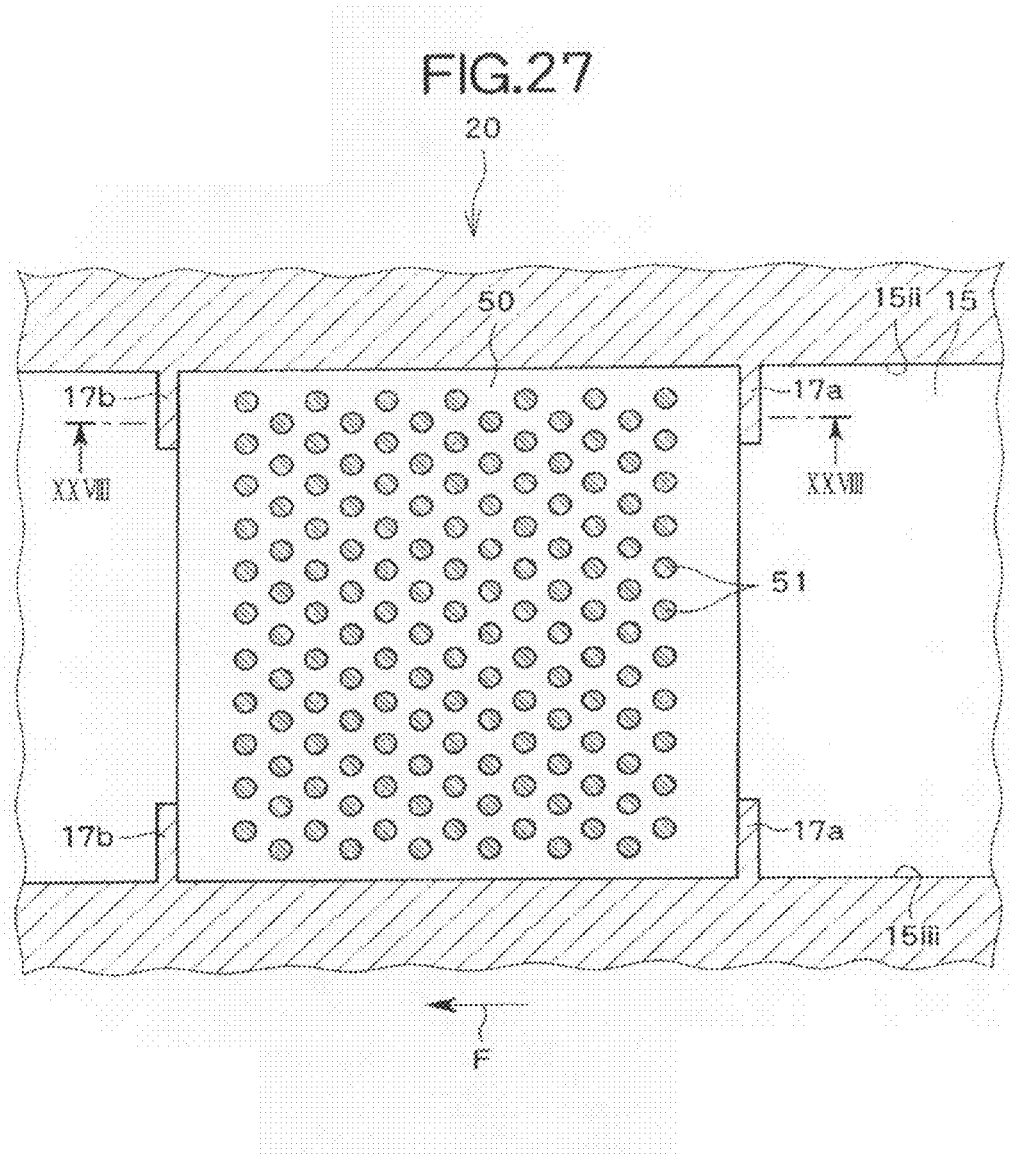
FIG. 27 is a plan view of an example of an electrochemical sensor device having dam portions according to the embodiment of the present invention.
Figure 28:
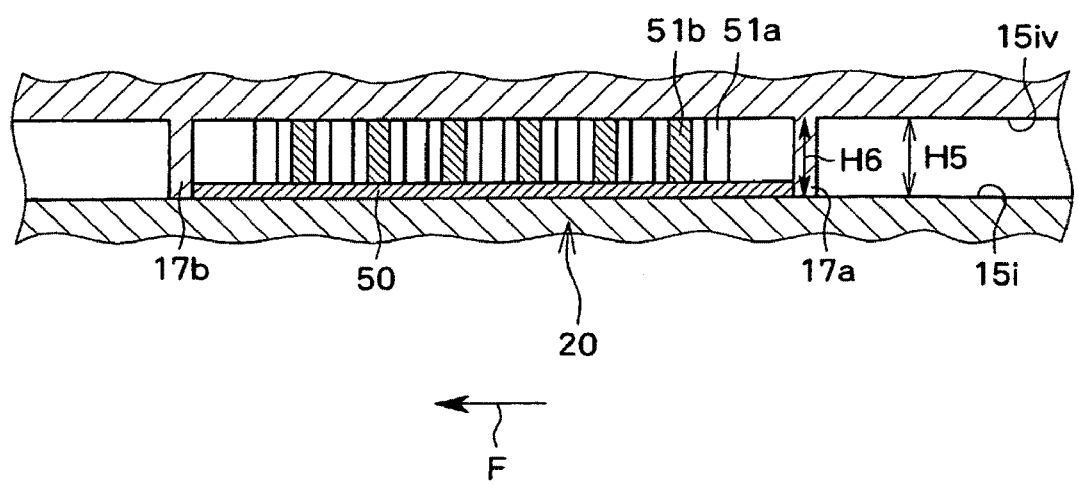
FIG. 28 is a sectional view of the electrochemical sensor device taken along the line XXVIII-XXVIII illustrated in FIG. 27.

In addition, as illustrated in FIGS. 27 and 28, when, in the device 1, a pair of upstream-side dam portions 17a is provided for the upstream end portion of the working electrode 20 and a pair of downstream-side dam portions 17b is provided for the downstream end portion of the working electrode 20, the effect of the protrusions 51 can be reliably obtained. FIG. 28 is a sectional view taken along the line XXVIII-XXVIII illustrated in FIG. 27.

As illustrated in FIGS. 27 and 28, the upstream-side dam portions 17a and the downstream-side dam portions 17b are each provided so as to block part of a flow in the longitudinal direction of the measuring portion 15.

In addition, one of the pair of the upstream-side dam portions 17a extends from the one side surface 15ii of the measuring portion 15, and the other of the pair extends from the other side surface 15iii of the measuring portion. In addition, one of the pair of the downstream-side dam portions 17b also extends from the one side surface 15ii of the measuring portion 15, and the other of the pair also extends from the other side surface 15iii of the measuring portion.

Providing the dam portions 17 described above can effectively prevent, for example, such passing of the analyte in a gap between each of the protrusion portions 51 and each of the side surfaces 15ii and 15iii as suggested by the result illustrated in FIG. 21B. Therefore, in this case, a large part of the analyte flowing into the working electrode 20 can be efficiently brought into contact with each of the protrusion portions 51.

In addition, the dam portions 17 do not necessarily need to be provided on the base 50. That is, in the example illustrated in each of FIGS. 27 and 28, the upstream-side dam portions 17a are provided so as to be adjacent to the upstream side of the working electrode 20, and the downstream-side dam portions 17b are provided so as to be adjacent to the downstream side of the working electrode 20. It should be noted that only the upstream-side dam portions 17a may be provided as the dam portions 17, and the downstream-side dam portions 17b may not be provided.

In addition, the dam portions 17 can be formed integrally with the channel substrate 2. That is, for example, when the channel substrate 2 is molded by the mold molding of a resin such as PDMS, the dam portions 17 can be simply formed simultaneously with the formation of the microchannel portion 10.

Then, when the channel substrate 2 having the dam portions 17 and the electrode substrate 3 on which the working electrode 20 is formed are stuck to each other while being properly aligned with each other, the device 1 in which the dam portions 17 are disposed at the upstream end portion and downstream end portion of the working electrode 20 can be produced simply and reliably.

Example 5

An effect of the formation of gold black on the surface of the working electrode 20 was identified. The flat working electrode 20 and the working electrode 20 having the pillars 51 each having a diameter of 30 μm were each produced in the same manner as in Example 4 described above, and gold black was formed on the surface of each of those working electrodes 20.

In other words, first, a reference electrode portion and a counter electrode portion produced on a substrate as described above were covered with a positive photoresist (S1818 manufactured by Rohm and Haas Electronic Materials LLC). After that, in a predetermined container, the substrate was immersed in an aqueous solution containing 83 mM of hydrogen tetrachloroaurate and 1.6 mM of lead acetate. In addition, the reference electrode portion of the substrate and the reference electrode and a platinum electrode were connected to a galvanostat (manufactured by HOKUTO DENKO CORPORATION). Then, a current density of −60 $\mu A/mm^2$ was applied for 5 minutes to form gold black in a working electrode portion. After that, the substrate was washed with acetone and subsequently with distilled water, and was then air-dried. Thus, a working electrode having gold black formed on its surface was formed.

Then, a value (μA) for a current flowing in each of the working electrodes 20 in association with the flow of ascorbic acid was measured with a sensor device provided with each of the working electrodes 20, in the same manner as in the above-mentioned example.

In FIG. 29, the axis of abscissa indicates the kind of the working electrode 20 and the axis of ordinate indicates a detected current value (μA). FIG. 29 confirmed that the formation of gold black on the surface of each of the flat working electrode 20 and the working electrode 20 having the pillars 51 improved measurement sensitivity.

In addition, the increase of the sensitivity attributable to the formation of gold black on the working electrode 20 having the pillars 51 was significant compared to that in the flat working electrode 20. The reason for the foregoing is probably as described below. In the working electrode 20 having the pillars 51, the solution in the microchannel portion 10 flows while colliding with the pillars 51, and hence an effect of increasing surface area by the formation of gold black on a surface area appears more significantly.

It should be noted that the device 1 is not limited to the above-mentioned examples. For example, the microchannel portion 10 is not limited to those described in the above-mentioned examples. That is, the microchannel portion 10 is not limited to one having the two inflow portions 11 and the two stem portions 12, and can have one or an arbitrary plurality of inflow portions 11 and one or an arbitrary plurality of stem portions 12. In addition, for example, the manner in which each channel portion in the microchannel portion 10 branches is not limited to such that one channel portion branches into two ways from its downstream end, and each channel portion can branch into three or more ways. In addition, the manner of the branching is not limited to such that one channel portion branches at right angles from its downstream end. For example, a plurality of branched channels can be formed so as to extend toward a downstream side while slanting so that a distance between them may increase. In addition, the device 1 is not limited to one constituted by combining the channel substrate 2 and the electrode substrate 3 formed as bodies separate from each other as described above. That is, for example, the device can be of such a constitution that the microchannel portion 10 and electrode systems are formed on one substrate, and the substrate is capped with the other substrate. In addition, the electrode systems such as the working electrodes 20 are not limited to ones formed on the bottom surface of the microchannel portion 10 as described above. That is, for example, at least part of the electrode systems, such as the working electrodes 20, can be formed on the side surfaces of the microchannel portion 10. In this case, at least part of the plurality of protrusion portions 51 of the working electrodes 20 can be formed in an entire region of the side surfaces of the channel, in the channel height direction, so as to extend in the width direction of the channel. In addition, the counter electrodes 31 and the reference electrodes 41 are not limited to ones formed individually in the respective measuring portions (such as the measuring portions 15, 16*a*, and 16*b* illustrated in each of FIGS. 1 to 3). That is, for example, the counter electrodes 31 can each be formed in a portion of the microchannel portion 10 other than the measuring portions.

The invention claimed is:

1. An electrochemical sensor device, comprising:
a channel portion formed in a substrate; and
working electrodes for subjecting an analyte in a solution flowing in the channel portion to electrochemical measurement,
wherein:
the channel portion includes
a first stem portion through which a first solution flows and a second stem portion through which a second solution flows, and
a plurality of measuring portions extending toward downstream sides of the first stem portion and the second stem portion and individually provided with the working electrodes;
the plurality of measuring portions include
a confluent portion through which a mixed solution of the first solution and the second solution flows, the confluent portion extending from a portion where a branch portion branching from the first stem portion and a branch portion branching from the second stem portion merge with each other toward a downstream side,
a first independent portion through which the first solution flows, the first independent portion extending toward the downstream side of the first stem portion without merging with any other channel, and
a second independent portion through which the second solution flows, the second independent portion extending toward the downstream side of the second stem portion without merging with any other channel; and
the working electrodes each have a plurality of conductive protrusion portions formed to protrude from a bottom surface of the measuring portion and disturbing the flows of the solutions flowing above the working electrodes, wherein:
the plurality of protrusion portions include
a plurality of plate-like protrusion portions each formed in a plate-like shape and crossing the measuring portion to block part of a flow in a longitudinal direction of the measuring portion and
a plurality of columnar protrusion portions each formed in a columnar shape;
the plurality of plate-like protrusion portions include
an upstream-side, plate-like protrusion portion and
a downstream-side, plate-like protrusion portion disposed on a downstream side of the upstream-side, plate-like protrusion portion; and
the plurality of columnar protrusion portions are disposed between the upstream-side, plate-like protrusion portion and the downstream-side, plate-like protrusion portion.

2. The electrochemical sensor device according to claim 1, wherein:
the plurality of measuring portions include a plurality of confluent portions through which mixed solutions, where the first solution and the second solution are mixed at different ratios from each other, flow; and
each of the plurality of confluent portions, the first independent portion, and the second independent portion is individually provided with one of the working electrodes.

3. The electrochemical sensor device according to claim 1, wherein the protrusion portions each have a height equal to or slightly lower than a height of the solution flowing above the working electrodes.

4. The electrochemical sensor device according to claim 1, wherein:
the plurality of plate-like protrusion portions include
a plurality of upstream-side, plate-like protrusion portions disposed in line with each other at predetermined intervals in a width direction of the measuring portion and
a plurality of downstream-side, plate-like protrusion portions disposed in line with each other at predetermined intervals in the width direction to block downstream sides of gaps between the plurality of upstream-side, plate-like protrusion portions on downstream sides of the plurality of upstream-side, plate-like protrusion portions; and
the plurality of columnar protrusion portions include
a plurality of upstream-side, columnar protrusion portions disposed between the plurality of upstream-side, plate-like protrusion portions and the plurality of downstream-side, plate-like protrusion portions, and disposed in line with each other at predetermined intervals in the width direction, and
a plurality of downstream-side, columnar protrusion portions disposed in line with each other at predetermined intervals in the width direction on downstream sides of the plurality of upstream-side, columnar protrusion portions.

5. The electrochemical sensor device according to claim 4, wherein the plurality of upstream-side, plate-like protrusion portions and the plurality of downstream-side, plate-like protrusion portions include a plate-like protrusion portion extending from one side surface of the measuring portion and a plate-like protrusion portion extending from the other side surface of the measuring portion, respectively.

6. The electrochemical sensor device according to claim 1, comprising:
a pair of upstream-side dam portions extending from one side surface and the other side surface of each of the measuring portions to block part of a flow in a longitudinal direction of the measuring portion in an upstream end portion of the working electrode; and
a pair of downstream-side dam portions extending from the one side surface and other side surface of the measuring portion to block part of the flow in the longitudinal direction of the measuring portion in a downstream end portion of the working electrode.

7. An electrochemical measuring method using the electrochemical sensor device according to claim 1, the method comprising electrochemically measuring the analyte in the solution flowing through each of the measuring portions in the electrochemical sensor device.

8. The electrochemical measuring method according to claim 7, further comprising:
preparing calibration data showing a correlation between a plurality of concentrations of the analyte and current values corresponding to the respective plurality of concentrations;

making the first solution containing the analyte flow into the first stem portion and making the second solution free of the analyte flow into the second stem portion; and determining a concentration of the analyte in the first solution on the basis of current values measured for the confluent portion, the first independent portion, and the second independent portion with the working electrodes, and the calibration data.

9. An electrode for an electrochemical sensor device, the electrode comprising:
   a plurality of conductive protrusion portions protruding from a bottom surface of a measuring portion of the electrode and configured to disturb the flow of solutions;
   said plurality of conductive protrusion portions comprising a plurality of plate-like protrusion portions each formed in a plate-like shape and crossing the measuring portion to block part of a flow in a longitudinal direction of the measuring portion, and a plurality of columnar protrusion portions each formed in a columnar shape;
   the plurality of plate-like protrusion portions include an upstream-side, plate-like protrusion portion and a downstream-side, plate-like protrusion portion disposed on a downstream side of the upstream-side, plate-like protrusion portion; and
   the plurality of columnar protrusion portions are disposed between the upstream-side, plate-like protrusion portion and the downstream-side, plate-like protrusion portion.

* * * * *

UNITED STATES PATENT AND TRADEMARK OFFICE
CERTIFICATE OF CORRECTION

PATENT NO.         : 8,303,800 B2
APPLICATION NO.    : 12/733533
DATED              : November 6, 2012
INVENTOR(S)        : Junji Fukuda et al.

Page 1 of 1

It is certified that error appears in the above-identified patent and that said Letters Patent is hereby corrected as shown below:

On the Title Page, please delete the following:

Item "(73)   Assignees:   University of Tsukuba, Ibaraki (JP);
                          Kuraray Co., Ltd., Okayama (JP)"

and replace with:

Item (73)   Assignees:   University of Tsukuba, Tsukuba-shi (JP);
                         Kuraray Co., Ltd., Kurashiki-shi (JP)

Signed and Sealed this
Eighteenth Day of March, 2014

Michelle K. Lee
*Deputy Director of the United States Patent and Trademark Office*